US010155951B2

(12) United States Patent
Yung et al.

(10) Patent No.: US 10,155,951 B2
(45) Date of Patent: Dec. 18, 2018

(54) METHODS AND SYSTEMS FOR ENGINEERING BACTERIAL SYSTEMS TO SHIELD TOXICITY DURING NON-NATIVE PROTEIN EXPRESSION AND PURIFICATION

(71) Applicant: LAWRENCE LIVERMORE NATIONAL SECURITY, LLC, Livermore, CA (US)

(72) Inventors: Mimi Cho Yung, Milpitas, CA (US); Feliza A. Bourguet, Livermore, CA (US); Timothy S. Carpenter, Livermore, CA (US); Matthew A. Coleman, Oakland, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 85 days.

(21) Appl. No.: 15/178,454

(22) Filed: Jun. 9, 2016

(65) Prior Publication Data
US 2016/0362697 A1 Dec. 15, 2016

Related U.S. Application Data

(60) Provisional application No. 62/173,272, filed on Jun. 9, 2015.

(51) Int. Cl.
*C12P 21/02* (2006.01)
*C12N 15/70* (2006.01)
*C07K 14/005* (2006.01)
*C12N 9/02* (2006.01)
*C12N 9/88* (2006.01)

(52) U.S. Cl.
CPC ............ *C12N 15/70* (2013.01); *C07K 14/005* (2013.01); *C12N 9/0008* (2013.01); *C12N 9/88* (2013.01); *C12P 21/02* (2013.01); *C12Y 102/01* (2013.01); *C12Y 403/01007* (2013.01); *C12N 2795/14222* (2013.01)

(58) Field of Classification Search
None
See application file for complete search history.

(56) References Cited

PUBLICATIONS

Lawrence et al. (2014) ACS Synth Biol., vol. 3, pp. 454-465. (Year: 2014).*
Reddy et al. (2004) International Journal of Antimicrobial Agents, vol. 24, pp. 536-547. (Year: 2004).*
Beeby, M. et al. "Growth and Localization of Polyhydroxybutyrate Granules in Ralstonia eutropha" Journal of Bacteriology, Mar. 2012, vol. 194, No. 5, pp. 1092-1099.
Beller, H. et al. "Identification of c-type cytochromes involved in anaerobic, bacterial U(IV) oxidation" Biodegradation, Jun. 2008, vol. 20, pp. 45-53.
Berneche, S. et al. "Energetics of ion conduction through the $K^+$ channel" Letters to Nature, Nov. 2001, vol. 414, pp. 73-77.
Bourguet, F. et al. "Characterization of a Novel Endolytic Protein, AMPD BCZK2532 as a Bacillus Anthracis Antimicrobial Protein" Applied and Environmental Microbiology, Mar. 2010, 36 pages.
Carpenter, T. et al. "Identification of a Possible Secondary Picrotoxin-Binding Site on the $GABA_A$ Receptor" Chemical Research in Toxicology, Sep. 2013, vol. 26, pp. 1444-1454.
Carpenter, T. et al. "A multidomain outer membrane protein from Pasteurella multocida: Modelling and simulation studies of PmOmpA" Biochimica et Biophysica Acta, 2007, pp. 2831-2840.
Carpenter, T. et al. "A Role for Loop F in Modulating GABA Binding Affinity in the $GABA_A$ Receptor" Journal of Molecular Biology, 2012, vol. 422, pp. 310-323.
Carpenter, T. et al. "Self-Assembly of a Simple Membrane Protein: Coarse-Grained Molecular Dynamics Simulations of the Influenza M2 Channel" Biophysical Journal, Oct. 2008, vol. 95, pp. 3790-3801.
Cho, M. et al. "Purification of polyhydroxybutyrate synthase from its native organism, Ralstonia eutropha: implications in the initiation and elongation of polymer formation in vivo" Biochemistry, Mar. 20, 2012, Author Manuscript, 30 pages.
Choudhary, S. et al. "Engineered Protein Nano-Compartments for Targeted Enzyme Localization" PLoS ONE, Mar. 2012, vol. 7, No. 3, 11 pages.
Chung, B. et al. "Crystal Structure of MraY, an Essential Membrane Enzyme for Bacterial Cell Wall Synthesis" Science, Aug. 30, 2013, Author Manuscript, 9 pages.
Cordova, E. et al. "The NRF2-KEAP1 Pathway Is an Early Responsive Gene Network in Arsenic Exposed Lymphoblastoid Cells" PLoS ONE, Feb. 2014, vol. 9, No. 2, 11 pages.
Doherty, A. et al. "Overproduction of the toxic protein, bovine pancreatic DNaseI, in *Escherichia coli* using a tightly controlled T7-promoter-based vector" Gene, 1993, vol. 136, pp. 337-340.
Dong, H. et al. "Gratuitous Overexpression of Genes in *Escherichia coli* Leads to Growth Inhibition and Ribosome Destruction" Journal of Bacteriology, Mar. 1995, vol. 177, No. 6, pp. 1497-1504.
Fan, C. et al. "Short N-terminal sequences package proteins into bacterial microcompartments" PNAS, Apr. 20, 2010, vol. 107, No. 16, pp. 7509-7514.
Gao, T. et al. "Characterization of De Novo Synthesized GPCRs Supported in Nanolipoprotein Discs" PLos ONE, Sep. 2012, vol. 7, No. 9, 9 pages.
Gaspar, D. et al. "From antimicrobial to anticancer peptides. A review" Frontiers in Microbiology, Oct. 2013, vol. 4, Article 294, 16 pages.
He, W. et al. "Controlling the diameter, monodispersity, and solubility of ApoA1 nanolipoprotein particles using telodendrimer chemistry" The Protein Society, Jun. 2013, vol. 22, pp. 1078-1086.
Hoskin, D. et al. "Studies on Anticancer Activities of Antimicrobial Peptides" Biochim. Biophys. Acta., Feb. 2008, Author Manuscript, 32 pages.
Khalid, S. et al. "OmpA: Gating and dynamics via molecular dynamics simulations" Biochemica et Biophysica Acta, 2008, pp. 1871-1880.

(Continued)

*Primary Examiner* — James S Ketter
(74) *Attorney, Agent, or Firm* — Steinfl + Bruno, LLP

(57) ABSTRACT

The invention described herein relates to methods, systems, compositions and cells to provide one or more toxic non-native proteins in a cell, wherein the one or more toxic non-native proteins are contained in at least one empty microcompartment within the cell.

27 Claims, 26 Drawing Sheets

Specification includes a Sequence Listing.

(56) References Cited

PUBLICATIONS

Khnouf, R. et al. "Cell-Free Expression of Soluble and Membrane Proteins in an Array Device for Drug Screening" Analytical Chemistry, Aug. 2010, vol. 82, No. 16, pp. 7021-7026.

Kim, D. et al. "Nanosensor dosimetry of mouse blood proteins after exposure to ionizing radiation" Scientific Reports, Jul. 2013, 8 pages.

Klingelhoefer, J. et al. "Peptide Nanopores and Lipid Bilayers: Interactions by Coarse-Grained Molecular-Dynamics Simulations" Biopyhsical Journal, May 2009, vol. 96, pp. 3519-3528.

Korendovych, I. et al. "Anion and Carboxylic Acid Binding to Monotopic and Ditopic Amidopyridine Macrocycles" J. Org. Chem, 2008, vol. 73, pp. 4771-4782.

Korendovych, I. et al. "Anion Binding to Monotopic and Ditopic Macrocyclic Amides" Organic Letters, 2006, vol. 8, No. 15, pp. 3171-3174.

Ly, S. et al. "Quantifying Membrane Protein Interactions in Solution using Fluorescence Correlation Spectroscopy" Biophysical Journal, Aug. 15, 2013, 11 pages.

Marr, A. et al. "Antibacterial peptides for therapeutic use: obstacles and realistic outlook" Current Opinion in Pharmacology, 2006, vol. 6, pp. 468-472.

Menzella, H. "Comparison of two codon optimization strategies to enhance recombinant protein production in *Escherichia coli*" Microbial Cell Factories, 2011, 8 pages.

Nguyen, L. et al. "The expanding scope of antimicrobial peptide structures and their modes of action" Trends in Biotechnology, Sep. 2011, vol. 29, No. 9, pp. 464-472.

Parachin, N. et al. "Expression systems for heterologous production of antimicrobial peptides" Peptides, 2012, vol. 38, pp. 446-456.

Parsons, J. et al. "Synthesis of Empty Bacterial Microcompartments, Directed Organelle Protein Incorporation, and Evidence of Filament-Associated Organelle Movement" Molecular Cell, Apr. 2010, vol. 38, pp. 305-315.

Rouse, S. et al. "Simulations of the BM2 Proton Channel Transmembrane Domain from Influenza Virus B" Biochemistry, Sep. 2009, vol. 48, pp. 9949-9951.

Sargent, F. et al. "A synthetic system for expression of components of a bacterial microcompartment" Microbiology, Sep. 2013, vol. 159, pp. 2427-2436.

Schmelcher, M. et al. "Bacteriophage endolysins as novel antimicrobials" Future Microbiology, Oct. 2012, Author Manuscript, 35 pages.

Sinha, S. et al. "The PduM Protein Is a Structural Component of the Microcompartments Involved in Coenzyme $B_{12}$-Dependent 1,2-Propanediol Degradation by *Salmonella enterica*" Journal of Bacteriology, Apr. 2012, vol. 194, No. 8, pp. 1912-1918.

Wang, G. et al. "APD3: the antimicrobial peptide database as a tool for research and education" Nucleic Acids Research, 2016, vol. 44, Database Issue, pp. D1087-D1093.

Wolfe, M. "Intramembrane-cleaving Proteases" Journal of Biological Chemistry, May 22, 2009, vol. 284, No. 21, pp. 13969-12973.

Wyrobek, A.J. et al. "Low dose radiation response curves, networks and pathways in human lymphoblastoid cells exposed from 1 to 10 cGy of acute gamma radiation" Mutation Research, Apr. 2011, vol. 722, pp. 119-130.

Yeates, T. et al. "Bacterial Microcompartment Organelles: Protein Shell Structure and Evolution" Annu. Rev. Biophys., Jun. 9, 2010, Author Manuscript, 25 pages.

Yeates, T. et al. "Protein-based organelles in bacteria: carboxysomes and related microcompartments" Nature Reviews: Microbiology, Sep. 2008, vol. 6, pp. 681-691.

Young, C. et al. "Recombinant protein expression and purification: A comprehensive review of affinity tags and microbial applications" Biotechnology Journal, 2012, vol. 7, pp. 620-634.

Yung, M.C. et al. "Biomineralization of uranium by PhoY phosphatase activity aids cell survival in Caulobacter crescentus" Applied and Environmental Microbiology, Mar. 26, 2014, 36 pages.

Yung, M.C. et al. "Shotgun Proteomic Analysis Unveils Survival and Detoxification Strategies by Caulobacter crescentus during Exposure to Uranium, Chromium, and Cadmium" Journal of Proteome Research, Feb. 21, 2014, vol. 13, No. 4, pp. 1833-1847.

Zhao, C. et al. "$GABA_A$ receptor target of tetramethylenedisulfotetramine" PNAS, Jun. 10, 2014, vol. 111, No. 23, pp. 8607-8612.

Arp, D.J. et al., "Molecular and Cellular Fundamentals of Aerobic Cometabolism of Trichloroethylene", Biodegradation 12, pp. 81-103, (2001).

Batoni, G. et al., "Antimicrobial Peptides and their Interaction with Biofilms of Medically Relevant Bacteria", Biochimica et Biophysica Acta 1858, pp. 1044-1060, (2016).

Bermudez-Humaran, L.G. et al., "Lactococci and Lactobacilli as Mucosal Delivery Vectors for Therapeutic Proteins and DNA Vaccines", Microbial Cell Factories 10, 10 pages, (2011).

Boman, H.G. et al., "Mechanisms of Action on *Escherichia coli* of Cecropin P1 and PR-39, Two Antibacterial Peptides from Pig Intestine", Infection and Immunity, vol. 61, No. 7, pp. 2978-2984, (1993).

Bourguet, F.A. et at, "Characterization of a Novel Lytic Protein Encoded by the Bacillus Cereus E33L Gene ampD as a Bacillus Anthracis Antimicrobial Protein", Applied and Environmental Microbiology, vol. 78, No. 8, pp. 3025-3027, (2012).

Canada, K.A. et al., "Directed Evolution of Toluene Ortho-Monooxygenase for Enhanced 1-Naphthol Synthesis and Chlorinated Ethene Degradation", Journal of Bacteriology, vol. 184, No. 2, pp. 344-349, (2002).

Carpenter T.S., et al., "Prediction of Blood-Brain Barrier Permeability of Drug-Like Compounds using Molecular Dynamics Simulations", Biophys. J,444-Pos, Board B199, (under review), (2014). 1 page.

Carson, B. et al., "Identification of Critical Amino Acids within the Nucleoprotein of Tacaribe Virus Important for Anti-Interferon Activity", Journal of Biological Chemistry, vol. 288, No. 12, pp. 8702-8711, (2013).

Chiu, W.A. et al., "Human Health Effects of Trichloroethylene: Key Findings and Scientific Issues", Environmental Health Perspectives, vol. 121, No. 3, pp. 303-311, (2013).

Cotruvo Jr., J.A. et al., "Metallation and Mismetallation of Iron and Manganese Proteins In Vitro and In Vivo: The Class I Ribonucleotide Reductases as a Case Study", Metallomics 4(10), pp. 1020-1036, (2012), 32 pages.

Darkoh, C. et al., "Toxin Synthesis by Clostridium Difficile Is Regulated through Quorum Signaling", Mbio, vol. 6, Issue 2, e02569-14, (2015), 10 pages.

Davis, J.H. et al., "Design, Construction, and Characterization of a Set of Insulated Bacterial Promoters", Nucleic Acids Research, vol. 39, No. 3, pp. 1131-1141, (2011).

De Lorenzo, V., "Systems Biology Approaches to Bioremediation", Current Opinion in Biotechnology, 19, pp. 579-689, (2008).

Durand, S. et al., "Activation of RegB Endoribonuclease by S1 Ribosomal Protein Requires an 11 nt Conserved Sequence", Nucleic Acids Research, vol. 34, No. 22, pp. 6549-6560, (2006).

Eddy, S.R. "Where did the BLOSUM62 Alignment Score Matrix Come From?", Nature Biotechnology, vol. 22, No. 8, pp. 1035-1036, (2004).

Eisenberg, S. et al., "PhiX174 Cistron A Protein is a Multifunctional Enzyme in DNA Replication", Proc. Natl. Acad. Sci. USA, vol. 74, No. 8, pp. 3198-3202, (1977).

Fujitani, S. et al., "Pneumonia Due to Pseudomonas Aeruginosa Part 1: Epidemiology, Clinical Diagnosis, and Source", Chest, 139(4), pp. 909-919, (2011).

Gao, T. et al., "Characterizing Diffusion Dynamics of a Membrane Protein Associated with Nanolipoproteins using Fluorescence Correlation Spectroscopy", Protein Science, vol. 20, pp. 437-447, (2011).

Giacalone, M.J. et al., "Toxic Protein Expression in *Escherichia coli* using a Rhamnose-Based Tightly Regulated and Tunable Promoter System", Biotechniques, vol. 40, No. 3, pp. 355-363, (2006).

(56) References Cited

PUBLICATIONS

Harrison, J.J. et al., "Microtiter Susceptibility Testing of Microbes Growing on Peg Lids: a Miniaturized Biofilm Model for High-Throughput Screening", Nature Protocols, vol. 5, No1. 7, pp. 1236-1254, (2010), 20 pages.
Hazen, T.C. et al., "Complexity of Groundwater Contaminants at DOE Sites", REP LBNL-4117E, Berkeley, CA 94720, (2008), 58 pages.
Keasling, J.D. "Synthetic Biology and the Development of Tools for Metabolic Engineering", Metabolic Engineering 14, pp. 189-195, (2012).
Krom, R.J. et al., "Engineered Phagemids for Nonlytic, Targeted Antibacterial Therapies", Nano Letters, 15, pp. 4808-4813, (2015).
Krumme, M.L. et al., "Degradation of Trichloroethylene by Pseudomonas Cepacia G4 and the Constitutive Mutant Strain G4 5223 PR1 in Aquifer Microcosms", Applied and Environmental Microbiology, vol. 59, No. 8, pp. 2746-2749, (1993).
Ly, S. et al., "Quantifying Interactions of a Membrane Protein Embedded in a Lipid Nanodisc using Fluorescence Correlation Spectroscopy", Biophysical Journal, vol. 106(2), L05-L08, (2014), 4 pages.
Mamat, U. et al., "Detoxifying *Escherichia coli* for Endotoxin-Free Production of Recombinant Proteins", Microbial Cell Factories, 14:57, (2015), 15 pages.
McGinness, K.E. et al., "Engineering Controllable Protein Degradation", Molecular Cell, 22, pp. 701-707, (2006).
Merritt, J.H. et al., "Growing and Analyzing Static Biofilms", Curr. Protoc Microbiol., Chapter 1, Unit-1B.1, (2005), 29 pages.
Morono, Y. et al., "Addition of Aromatic Substrates Restores Trichloroethylene Degradation Activity in Pseudomonas Putida F1", Applied and Environmental Microbiology, vol. 70, No. 5, pp. 2830-2835, (2004).
Newman, L.M. et al., "Trichloroethylene Oxidation by Purified Toluene 2-Monooxygenase: Products, Kinetics, and Turnover-Dependent Inactivation", Journal of Bacteriology, vol. 179, No. 1, pp. 90-96, (1997).
Purnick, P.E. et al., "The Second Wave of Synthetic Biology: From Modules to Systems", Nat Rev Mol Cell Biol., vol. 10, pp. 410-422, (2009), 14 pages.
Quin, M.B. et al., "Designer Microbes for Biosynthesis", Curr Opin Biotechnol., pp. 55-61, (2014), 14 pages.
Rhodius, V.A. et al., "Design of Orthogonal Genetic Switches Based on a Crosstalk Map of Sigmas, Anti-Sigmas, and Promoters", Molecular Systems Biology 9, Article No. 702, (2013), 13 pages.
Riley, R.G. et al., "Chemical Contaminants on DOE lands and Selection of Contaminant Mixtures for Subsurface Science Research", REP DOE/ER-0547t, Washington, D.C., (1992), 80 pages.
Rui, L.Y. et al., "Metabolic Pathway Engineering to Enhance Aerobic Degradation of Chlorinated Ethenes and to Reduce their Toxicity by Cloning a Novel Glutathione S-Transferase. An Evolved Toluene O-Monooxygenase, and Gamma-Glutamylcysteine Synthetase", Environmental Microbiology, 6(5), pp. 491-500, (2004).
Rutherford, S.T. et al., "Bacterial Quorum Sensing: Its Role in Virulence and Possibilities for its Control", Cold Spring Harbor Perspectives in Medicine, 2, (2012), 26 pages.
Saeidi, N. et al., "Engineering Microbes to Sense and Eradicate Pseudomonas Aeruginosa, a Human Pathogen", Molecular Systems Biology 7, Article 521, (2011), 11 pages.
Salts, H.M. et al., "Automated Design of Synthetic Ribosome Binding Sites to Precisely Control Protein Expression", Nat. Biotechnol., 27(10), pp. 946-950, (2009), 19 pages.
Scott, M.G. et al., "Biological Properties of Structurally Related Alpha-Helical Cationic Antimicrobial Peptides", Infection and Immunity, vol. 67, No. 4, pp. 2005-2009, (1999).
Shaner, N.C. et al., "A Guide to Choosing Fluorescent Proteins", Nature Methods, vol. 2, No. 12, pp. 905-909, (2005), 11 pages.
Sun, A.K. et al., "Trichloroethylene Degradation and Mineralization by Pseudomonads and Methylosinus Trichosporium OB3B", Appl Microbial Biotechnol., 45, pp. 248-256, (1996).
Van De Loosdrecht, A.A. et al., "A Tetrazolium-Based Colorimetric MTT Assay to Quantitate Human Monocyte Mediated Cytotoxicity against Leukemic Cells From Cell Lines and Patients with Acute Myeloid Leukemia", Journal of Immunological Methods 174, pp. 311-320, (1994).
Van Hylckama Vlieg, J.E. et al., "Formation and Detoxification of Reactive Intermediates in the Metabolism of Chlorinated Ethenes", Journal of Biotechnology 85, pp. 81-102, (2001).
Volzing, K. et al., "Antimicrobial Peptides Targeting Gram-Negative Pathogens, Produced and Delivered by Lactic Acid Bacteria", ACS Synth Biol., 2(11), pp. 643-650, (2013), 20 pages.
Whitechurch, C.B. et al., "Extracellular DNA Required for Bacterial Biofilm Formation", Science, vol. 295, p. 1487, (2002).
Wood, T.K., "Molecular Approaches in Bioremediation", Current Opinion in Biotechnology, 19, pp. 572-578, (2008).
Yeager, C.M. et al., "Cytotoxicity Associated with Trichloroethylene Oxidation in Burkholderia Cepaci G4", Applied and Environmental Microbiology, vol. 67, No. 5, pp. 2107-2115, (2001).
Zhang, L. et al., "Antimicrobial Peptide Therapeutics for Cystic Fibrosis", Antimicrobial Agents and Chemotherapy, vol. 49, No. 7, pp. 2921-2927, (2005).
Zhang, G. et al., "Extracellular Accumulation of Recombinant Proteins Fused to the Carrier Protein YebF in *Escherichia coli*", Nature Biotechnology, vol. 24, No. 1, pp. 100-104, (2006).
Zylstra, G.J. et al., "Trichloroethylene Degradation by *Escherichia coli* Containing the Cloned Pseudomonas Putida F1 Toluene Dioxygenase Genes", Applied and Environmental Microbiology, vol. 55, No. 12, pp. 3162-3166, (1989).
Gupta, S. et al., "Genetically Programmable Pathogen Sense and Destroy", ACS Synth. Biol., 2, pp. 715-723, (2013).
Hwang, I.Y. et al., "Reprogramming Microbes to be Pathogen-Seeking Killers", ACS Synth. Biol., 3, pp. 228-237, (2014).
Kim, E.Y. et al., "A Rapid Flow Cytometry Assay for the Relative Quantification of Protein Encapsulation into Bacterial Microcompartments", Biotechnol. J., 9, pp. 348-354, (2014). 8 pages.
Li, W-F. et al., "Apidaecin-Type Peptides: Biodiversity, Structure-Function Relationships and Mode of Action", Peptides 27, pp. 2350-2359, (2006).
Moon, H. et al., "Developing Genetically Engineered Encapsulation Protein Cage Nanoparticles as a Targeted Delivery Nanoplatform", Biomacromolecules, 15, pp. 3794-3801, (2014).
Newman, L.M. et al., "Purification and Characterization of Toluene 2-Monooxygenase from Burkholderia Cepacia G4", Biochemistry, 34, pp. 14066-14076, (1995).
Pieper, D.H. "Aerobic Degradation of Polychlorinated Biphenyls", Appl. Microbiol. Biotechnol., 67, pp. 170-191, (2005).
Schechter, I. et al., "On the Size of the Active Site in Proteases. I. Papain", Biochemical and Biophysical Research Communications, vol. 27, No. 2, pp. 157-162, (1967).
Schechter, I. et al., "On the Active Site of Proteases. III. Mapping the Active Site of Papain; Specific Peptide Inhibitors of Papain", Biochemical and Biophysical Research Communications, vol. 32, No. 5, pp. 898-902, (1968).
Sutter, M. et al., "Structural Basis of Enzyme Encapsulation into a Bacterial Nanocompartment", Nature Structural & Molecular Biology, vol. 15, No. 9, pp. 939-947, (Sep. 2008).
Wong, T.Y. et al., "Alginate Lyase: Review of Major Sources and Enzyme Characteristics, Structure-Function Analysis, Biological Roles, and Applications", Annu. Rev. Microbiol., 54, pp. 289-340, (2000), 55 pages.
Worsdorfer, B. et al., "Directed Evolution of a Protein Container", Science, vol. 331(6017), pp. 589-592, (2011), 5 pages.

\* cited by examiner

METHODS AND SYSTEMS FOR ENGINEERING BACTERIAL SYSTEMS TO SHIELD TOXICITY DURING NON-NATIVE PROTEIN EXPRESSION AND PURIFICATION

CROSS REFERENCE TO RELATED APPLICATIONS

The present application claims priority to U.S. provisional application No. 62/173,272, entitled "Engineering Bacterial Systems to Shield Toxicity During Non-Native Protein Expression and Purification" filed on Jun. 9, 2015, which is incorporated by reference in its entirety.

STATEMENT OF GOVERNMENT GRANT

The United States Government has rights in this invention pursuant to Contract No. DE-AC52-07NA27344 between the United States Department of Energy and Lawrence Livermore National Security, LLC, for the operation of Lawrence Livermore National Laboratory.

FIELD

The present disclosure relates to protein production in cell systems and in particular to engineering bacterial systems to shield toxicity during non-native protein expression and purification and related cells, compositions, methods and systems.

BACKGROUND

Production of non-native, cytotoxic proteins has been the subject of research in several fields, including commercial and academic fields in connection with non-native protein production applications.

Despite the presence of various approaches, expression, production and/or purification of cytotoxic proteins for various uses is still challenging.

SUMMARY

Provided herein, are methods and systems and related compositions and cells that can be used in several embodiments to shield bacteria from toxicity during non-native protein expression, production and/or purification.

According to a first aspect, a method to provide a toxic non-native protein in a cell is described. The method comprises introducing into the cell at least one first polynucleotide encoding at least one microcompartment protein, the at least one polynucleotide operatively linked to one or more first regulatory elements leading to the expression of the at least one microcompartment protein in the cell, the at least one microcompartment protein capable of assembling with one or more same and/or different microcompartment proteins to form at least one empty microcompartment within the cell; and introducing into the cell at least one second polynucleotide encoding for one or more toxic non-native proteins capable of reacting with a native membrane substrate with a reaction resulting in a cell damage, each of the one or more toxic non-native proteins operably linked to a leader peptide capable of directing expressed proteins to the at least one empty microcompartment, the at least one second polynucleotide operably linked to one or more second regulatory elements leading to the expression of the at least one toxic non-native protein operably linked to the leader peptide in the cell, to obtain the one or more toxic non-native protein capable of reacting with a native membrane proteins within the at least one empty microcompartment within the cell.

According to a second aspect, a system for shielding a bacterial cell from toxicity during intracellular production of a toxic non-native protein is described. The system comprises at least one first polynucleotide encoding at least one microcompartment protein operatively linked to one or more first regulatory elements leading to the expression of the at least one microcompartment protein in the cell, the at least one microcompartment protein capable of assembling with one or more same and/or different microcompartment proteins to form at least one empty microcompartment within the cell; and at least one second polynucleotide encoding for at least one toxic non-native protein capable of reacting with a native membrane substrate with a reaction resulting in a cell damage, each of the one or more toxic non-native proteins operably linked to a leader peptide capable of directing expressed proteins to the at least one empty microcompartment, the at least one second polynucleotide operatively linked to one or more second regulatory elements leading to the expression of the at least one toxic non-native protein operably linked to the leader peptide. In the embodiments described, polynucleotides described in the systems are used either simultaneously or sequentially in the methods to provide one or more toxic non-native proteins in a cell.

According to a third aspect, a cell obtained by the methods to provide one or more toxic non-native proteins and/or systems for shielding a bacterial cell from toxicity during intracellular production of a toxic non-native protein is described.

According to a fourth aspect, a cell comprising at least one toxic non-native protein within at least one microcompartment within the cell is described.

According to a fifth aspect, a composition is described. The composition comprises one or more cells obtained by the methods to provide one or more toxic non-native proteins and/or systems for shielding a bacterial cell from toxicity during intracellular production of a toxic non-native protein described, together with a suitable vehicle. The composition can alternatively or additionally include one or more cells comprising at least one toxic non-native protein within at least one microcompartment within a cell.

According to a sixth aspect, a method to produce a toxic protein is described. The method comprises introducing at least one first polynucleotide into a cell, the at least one first polynucleotide encoding at least one microcompartment protein, and wherein the at least one polynucleotide is operatively linked to one or more first regulatory elements leading to the expression of the at least one microcompartment protein in the cell, the at least one microcompartment protein capable of assembling with one or more same and/or different microcompartment proteins to form at least one empty microcompartment within the cell; and introducing at least one second polynucleotide into the cell, the at least one second polynucleotide encoding for one or more toxic non-native proteins capable of reacting with a native-membrane proteins, each toxic non-native proteins operably linked to a leader peptide capable of directing expressed proteins to the at least one empty microcompartment, the at least one second polynucleotide operably linked to one or more second regulatory elements leading to the expression of the at least one toxic non-native protein operably linked to the leader peptide in the cell, to obtain the one or more toxic proteins within the at least one microcompartment in the cell. The method further comprises isolating the one or more toxic non-native proteins from the at least one microcompartment in the cell.

Methods and systems herein described and related cells and compositions can be used in some embodiments in connection with production of cytotoxic proteins or precursor thereof.

Methods and systems herein described and related cells and compositions can be used in some embodiments in connection with expression in cells of non-native cytotoxic proteins or precursor thereof.

Methods and systems herein described and related cells and compositions can be used in some embodiments in connection with production in cells of non-native cytotoxic proteins or precursor thereof.

Methods and systems herein described and related cells and compositions can be used in some embodiments in connection with purification of non-native cytotoxic proteins or precursor thereof from cells.

Methods and systems herein described and related cells and compositions can be applied in several fields, including basic biology research, applied biology, bio-engineering, bio-energy, medical research, medical diagnostics, therapeutics, bio-fuels, and in additional fields where cytotoxic proteins and/or their precursors can be used.

The details of one or more embodiments of the disclosure are set forth in the accompanying Appendix A, incorporated herein by reference in its entirety and the description below. Other features, objects, and advantages will be apparent from Appendix A, the following description, and the claims.

BRIEF DESCRIPTION OF DRAWINGS

The accompanying drawings, which are incorporated into and constitute a part of this specification, illustrate one or more embodiments of the present disclosure and, together with detailed description and the examples, serve to explain the principles and implementations of the disclosure.

FIG. 1A shows the transmission electron micrograph of Halothiobacillus neapolitanus cells containing carboxysomes (arrows). Scale bar, 100 nm. FIG. 1B shows a 3D model of a BMC shell

DETAILED DESCRIPTION

Figure 1A:
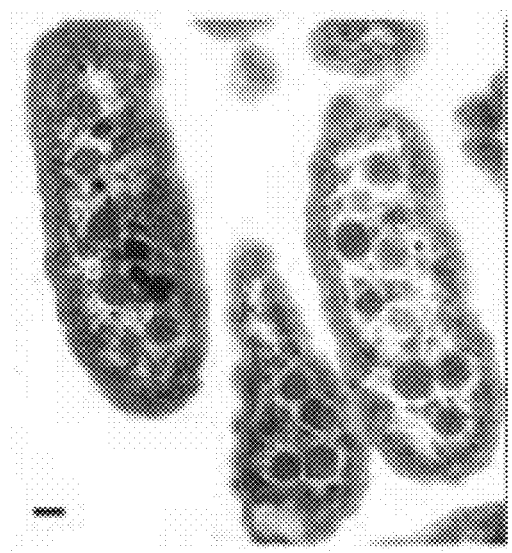
FIGS. 1A-B from references [1] and [2] show in some embodiments bacterial microcompartments.

Provided herein are methods and systems and related compositions and cells that can be used in several embodiments to shield bacteria from toxicity during expression, production and/or purification of certain toxic non-native protein. In particular, provided herein are methods and systems and related compositions and cell that allow compartmentalization of certain toxic non-native proteins in cells thus shielding the cell from toxicity from said toxic non-native proteins.

The wording "native" as used herein with reference to a compound and a cell, identifies a compound, molecule or structure naturally provided and in particular produced in the cell. Therefore a native protein or a native substrate when described in connection with a cell, refers to a protein and/or substrate that is itself naturally provided and in particular, produced in the referenced cell. Conversely, the term "non-native" as used herein with reference to a protein and/or a substrate in connection with a cell, refers to a protein and/or substrate that is itself not naturally produced in the referenced cell.

As used throughout, a "toxic non-native protein" refers to a protein or peptide that is itself not naturally produced by a cell and is toxic to the cell when provided or produced in said cell.

In particular toxic non-native proteins in the sense of the disclosure in connection with cells where they are provided or produced indicates proteins or peptides that are not native to said cell and can react with a native cellular target substrate to provide cell damage by triggering a series of linked biological or chemical reactions within the cell resulting in damage to said cell.

The wording "native cellular target substrate" or "native cellular substrate' as used herein indicates a compound molecule or structure that is naturally occurring in a cell and is a part of reactions taking place in the cell to keep the cell alive. Exemplary native cellular target substrates in the sense of the disclosure comprise native cellular lipids, proteins, nucleic acids and/or related cellular structures, such as cell membrane or cell chromatin.

Exemplary reactions between a native cellular target substrate and a toxic non-native protein, which exemplary reactions trigger a series of linked biological or chemical reactions in the cell resulting in a damage to the cell, comprise binding and/or bond cleavage resulting in disruption and/or inactivation of the cellular target substrate. For example targeting of membrane lipids damages the cell membrane which, on its turn, impacts the state of cell electrolytes, e.g. calcium, which when constantly increased, induces apoptosis.

The word "damage" as used herein refers to a physical harm caused to a cell in such a way as to impair its normal function. In particular, cell damage can occur as a result of disruption the normal homeostasis of an affected cell. Among other causes, cell damage can be due to physical, chemical, or, biological, factors resulting from targeting of cell components such as DNA and the cell membrane. Cell damage can be reversible or irreversible. Depending on the extent of injury, the cellular response may be adaptive and where possible, homeostasis is restored. Cell death occurs when the severity of the injury exceeds the cell's ability to repair itself and can occur by necrosis or apoptosis.

Toxicity in the sense of the disclosure in particular occurs when a non-native protein interferes with the normal proliferation and homeostasis of the microorganism and the visible result is slower growth rate, low final cell density, and death ([3]-[4]) Toxicity of a non-native protein can therefore be detected with reference cell growth before production of a non-native toxic protein (basal growth) and after detection of possible toxicity of vectors or other expression system for production of the non-native protein within a cell which can be performed with approaches discussed for example in reference (2) or otherwise identifiable by a skilled person upon reading of the present disclosure. After control of basal growth and of toxicity of the expression system, the culture can be grown until the expression of the non-native protein. Following expression of the non-native protein, if the non-native protein is toxic, cell growth will be impaired or arrested depending on the level of toxicity. In some cases, the level of toxicity of a non-native protein can be dependent on a threshold of host tolerance. In such situations, toxicity of a non-native protein can be dependent on the level of expression of the non-native protein in comparison with the threshold of host tolerance which should be reached and exceeded for the protein to have toxicity as will be understood by a skilled person.

Examples of proteins or peptides that are toxic and therefore harmful to a cell include antimicrobial peptides, as well as proteases and lysins, which are harmful to bacterial cells through direct targeting of cytoplasmic, membrane, DNA or protein synthesis.

In particular, toxic non-native protein that can be used in methods and systems and in related cells and compositions of the instant disclosure, are toxic proteins or peptides that are non-native to the cell where they are produced and that have a native cellular target substrate which is a native membrane substrate.

The wording "membrane" as used herein indicates a biological membrane that separates the interior of a cell from the outside environment and can have different structure and configurations in different type of cells as will be understood by a skilled person. In particular, the wording "membrane" as used herein is intended to encompass: i) a cell plasma membrane (also identified as inner membrane in Gram negative bacteria) typically formed by a phospholipid bilayer with embedded proteins, ii) the outer membrane of Gram-negative bacteria formed by a phospholipid bilayer with embedded proteins different in composition from the inner membrane (e.g. rich in lipopolysaccharide), as well as iii) the cell wall, a structural layer that surrounds some types of cells, situated outside the cell membrane and is mainly composed of peptidoglycan (amino acids and sugars). In particular, cell wall can be made of peptidoglycan (also called murein), which is made from polysaccharide chains cross-linked by unusual peptides containing D-amino acids.

The wording "native membrane substrate" as used herein indicates a compound that is naturally located in the membrane of a cell in the sense of the disclosure and in particular in the membrane of the cell where the toxic non-native protein is expressed or to be expressed. Native membrane substrates comprise proteins, peptidoglycans, and lipids located in the plasma membrane, inner membrane, outer membrane or cell wall of a cell in the sense of the disclosure.

An exemplary native membrane substrate that can be targeted by toxic proteins herein described are peptidoglycan and lipopolysaccharide (LPS) biosynthesis proteins, which are enzymes such as MraY, LpxK, KdtA, LpxL LpxM, MraG, FtsW catalyzing biosynthesis of peptidoglycans of the cell wall and LPS in the outer membrane. In particular MraY (phospho-MurNAc-pentapeptide translocase) is an integral membrane enzyme that catalyzes an essential step of bacterial cell wall biosynthesis: the transfer of the peptidoglycan precursor phospho-MurNAc-pentapeptide to the lipid carrier undecaprenyl phosphate ([5]) Non-native toxic proteins such as LysE react with peptidoglycan with resulting damage to the cell wall and to the cell. LpxK is a gene encoding tetraacyldisaccharide 4'-kinase, an enzyme that phosphorylates the 4'-position of a tetraacyldisaccharide 1-phosphate precursor (DS-1-P) of lipopolysaccharide lipid A. This enzyme belongs to the family of transferases, specifically those transferring phosphorus-containing groups (phosphotransferases) with an alcohol group as acceptor. KdtA is a gene encoding 3-deoxy-D-manno-octulosonic acid transferase, which is involved in lipopolysaccharide (LPS) biosynthesis. This enzymes catalyzes the transfer of two 3-deoxy-D-manno-octulosonate (Kdo) residues from CMP-Kdo to lipid IV(A), the tetraacyldisaccharide-1,4'-bisphosphate precursor of lipid A. LpxM is a gene encoding Lipid A biosynthesis myristoyltransferase, an enzyme that catalyzes the transfer of myristate from myristoyl-acyl carrier protein (ACP) to Kdo(2)-(lauroyl)-lipid IV(A) to form Kdo(2)-lipid A. In vitro, the protein can acylate Kdo(2)-lipid IV(A), but the acylation of (Kdo)2-(lauroyl)-lipid IV(A) is about 100 times faster. In vitro, the protein can use lauroyl-ACP but displays a slight kinetic preference for myristoyl-ACP. LpxL is a gene encoding Lipid A biosynthesis lauroyltransferase, an enzyme that catalyzes the transfer of laurate from lauroyl-acyl carrier protein (ACP) to Kdo(2)-lipid IV(A) to form Kdo(2)-(lauroyl)-lipid IV(A). This enzyme has 10 fold selectivity for lauroyl-ACP over myristoyl-ACP. In vitro, this enzyme can also catalyze a slow second acylation reaction leading to the formation of Kdo(2)-(dilauroyl)-lipid IV(A). FtsW is a gene encoding lipid II flippase FtsW protein, a cell division protein that transports lipid-linked peptidoglycan precursors from the inner to the outer leaflet of the cytoplasmic membrane. This protein is required for localization of FtsI, and may also play a role in the stabilization of the FtsZ ring during cell division.

Additional, native membrane substrates that can be targeted by native toxic proteins herein described are peptidoglycans comprising a pentapeptide motif A(D/N)LXX (SEQ ID NO: 1), where X can be any amino acid with the central position in the pentapeptide motif (also designated as position i) being usually a leucine, position i–2 being usually an alanine and the two subsequent positions (i+1 and i+2) configured so that the side chains of positions i–2 and i point into the hydrophobic interior of the protein while the side chains of positions i–1, i+1 and i+2 are exposed on the surface of the proteins. Those peptidoglycans can be targeted for example by non-native lysin proteins with a peptidase domain which can be identified for example using a BLAST search on NCBI. For instance Ply500 has a pfam02557: VanY: D-alanyl-D-alanine carboxypeptidase motif which would react with a pentapeptide motif in a peptidoglycan. Additional lysins can be identified by a skilled person upon reading of the present disclosure.

Further native membrane substrates that can be targeted by native toxic proteins are peptidoglycans comprising a sugar motif, such as GlcNAc-X-GlcNAc with X being any amino acid and other sugar motifs identifiable by a skilled person. These native membrane substrate can be targeted by non-native lysins proteins having an amidase domain, which can also be identified for example using a BLAST search, and additional lysins identifiable by a skilled person.

Additional native membrane substrates that can be targeted by native toxic proteins herein described are phospholipids in the inner membrane. In those embodiments, one or more non-native toxic proteins can bind to lipid and inhibit proper structure of the lipid bilayer membrane, causing holes to form in the membrane. Examples of toxic proteins targeting phospholipids are AMPs having alpha helical or beta-sheet that disrupt inner membrane such as cecropin, magainin, melittin, and protegrin I.

Further native membrane substrates that can be targeted by native toxic proteins are lipids in the outer membrane (e.g., Lipid II and LPS). Examples of toxic proteins targeting lipids of the outer membrane comprise cationic antimicrobial peptides such as cecropin P1, defensins, and nisins.

Additional native membrane substrates that can be targeted by native toxic proteins herein described are outer membrane proteins such as integral outer membrane proteins folding into antiparallel beta-barrels. (e.g. proteins belonging to the OmpA membrane domain, the OmpX protein, phospholipase A, general porins (OmpF, PhoE), substrate-specific porins (LamB, ScrY) and the TonB-dependent iron siderophore transporters FhuA and FepA). Examples of toxic proteins targeting lipids of the outer membrane proteins are cationic antimicrobial peptides. An example is inhibition of OmpF porin by HP(2-20) peptide. Additional cationic antimicrobial peptides expected to be found in ([6] [7]).

In some embodiments, the non-native toxic proteins are expressed in constructs where the toxic protein is fused to a leader tag, which is later cleaved thus activating the non-native toxic protein. In those embodiments, the presence of the leader tag can inactivate the toxic protein at least in part the toxic proteins makes the toxic protein unavailable to act on the native target membrane substrate In some embodiments, "toxic non-native protein" that can be used in methods and systems and in related cells and compositions of the instant disclosure comprise antimicrobial peptides targeting cell membrane, proteases targeting proteins in a native cell membrane as defined herein, and lysins as will be understood by a skilled person.

The term "Antimicrobial peptides" or "AMPs", indicates peptides generally less than 200 amino acids and typically between 12 and 50 amino acids, having two or more positively charged residues provided by arginine, lysine or, in acidic environments, histidine, and a large proportion (generally >50%) of hydrophobic residues and having an antimicrobial activity as would be understood by a skilled person. The secondary structures of AMPs typically follow 4 themes, including i) α-helical, ii) β-stranded due to the presence of 2 or more disulfide bonds, iii) β-hairpin or loop due to the presence of a single disulfide bond and/or cyclization of the peptide chain, and iv) extended as would be understood by a skilled person. The final cellular configuration of AMPs typically contains hydrophilic amino acid residues aligned along one side and hydrophobic amino acid residues aligned along the opposite side of a helical molecule. AMPs can provide cell damage by reacting with membrane components to provide membrane permeabilization or with a range of cytoplasmic targets. In some instances, AMPs amino acid composition, amphipathicity, cationic charge and size allow them to attach to and insert into membrane bilayers to form pores by 'barrel-stave', 'carpet' or 'toroidal-pore' mechanisms. In some instances, AMPs can bind target intracellular molecules which are crucial to cell living thus resulting in cell damage through inhibition of cell wall synthesis, alteration of the cytoplasmic membrane, activation of autolysin, inhibition of DNA, RNA, and protein synthesis, and/or inhibition of enzymes identifiable by a skilled person. In general the antimicrobial activity of these peptides is determined by measuring the minimal inhibitory concentration (MIC), which is the lowest concentration of drug that inhibits bacterial growth. Antimicrobial peptides have been demonstrated to kill Gram negative and Gram positive bacteria, enveloped viruses, fungi and even transformed or cancerous cells.

In some embodiments, AMPs that can be produced or provided in a cell according to methods and systems of the disclosure and related cell and compositions comprise cationic AMPs that target phospholipids in the inner membrane, such as cecropin, magainin, melittin, and protegrin 1, or derivatives thereof.

In some embodiments, AMPs that can be produced or provided in a cell according to methods and systems of the disclosure and related cell and compositions comprise cationic AMPs that target lipids in a native outer membrane (e.g., Lipid II, LPS). Examples include cecropin P1, defensins, and nisins, or derivatives thereof In some embodiments, AMPs that can be produced or provided in a cell according to methods and systems of the disclosure and related cell and compositions comprise cationic AMPs that target native outer membrane proteins, such as HP(2-20) peptide capable of targeting and inhibiting OmpF porin as well as SMAP-29 and CAP-18 both capable of targeting and inhibiting outer membrane protein I (OprI)

In particular, the term "cecropins" indicate AMPs of about 31-37 amino acid residues having alpha helical conformation and being capable of targeting native membrane substrates of both Gram-positive and Gram-negative bacteria. Cecropins isolated from insects other than Hyalophora cecropia (Cecropia moth) are also known as bactericidin, lepidopterin, sarcotoxin, and additional names identifiable by a skilled person. Exemplary cecropin comprise Cecropin A (KWKLFKKIEKVGQNIRDGIIKAGPAVAVVGQATQ-IAK SEQ ID NO:2) having a secondary structure with two a helices, and being capable of forming a ion channels at low peptide to lipid ratios and pores at high peptide to lipid ratios as will be understood by a skilled person. Exemplary cecropins also comprise: Cecropin B (KWKVFKKIEK-MGRNIRNGIVKAGPAIAVLGEAKAL SEQ ID NO:3) having two a helices in the secondary structure, CECD from *Aedes aegypti* (Yellowfever mosquito), Papiliocin (A lepidopteran) from *Papilio xuthus* an Asian swallowtail butterfly, and Cecropin P1, an antibacterial peptide from *Ascaris suum*, a parasitic nematode that resides in the pig intestine. Cecropin derivatives comprise peptides modified cecropins (e.g. cecropin A, and cecropin B). In some embodiments, derivatives of cecropins have anticancer properties and are called anticancer peptides (ACPs) ([8] In particular hybrid ACPs based on Cecropin A have been studied for anticancer properties ([9])

The term "magainins" indicate a class of antimicrobial peptides found in the African clawed frog *Xenopus laevis* identifiable by a skilled person The term "melittin" indicates the principal active component of apitoxin (bee venom), a powerful stimulator of phospholipase A2 as will be understood by a skilled person. Melittin is a peptide consisting of 26 amino acids with the sequence GIGAVLKVLTTGLPALISWIKRKRQQ (SEQ ID NO: 4).

The term "protegrins" indicates small peptides containing 16-18 amino acid residues. The amino acid composition of protegrins contains six positively charged arginine residues and four cysteine residues. Their secondary structure is classified as cysteine-rich β-sheet antimicrobial peptides, AMPs that display limited sequence similarity to certain defensins and tachyplesins. In solution, the peptides fold to form an anti-parallel β-strand with the structure stabilized by two cysteine bridges formed among the four cysteine residues. Protegrins bind to lipopolysaccharide, a property that may help them to insert into the membranes of gram-negative bacteria and permeabilize them. The term "defensins" as used herein identifies small cysteine-rich cationic proteins found in vertebrates, invertebrates and plants. Defensins have 18-45 amino acids including six to eight conserved cysteine residues. Most defensins function by binding to the microbial cell membrane, and, once embedded, forming pore-like membrane defects that allow efflux of essential ions and nutrients.

The term "nisins" as used herein identifies a polycyclic peptide produced by the bacterium *Lactococcus lactis* having 34 amino acid residues, including the uncommon amino acids lanthionine (Lan), methyllanthionine (MeLan), didehydroalanine (Dha), and didehydroaminobutyric acid (Dhb). These unusual amino acids are introduced by posttranslational modification of the precursor peptide. In these reactions, a ribosomally synthesized 57-mer is converted to the final peptide. The unsaturated amino acids originate from serine and threonine, and the enzyme-catalysed addition of cysteine residues to the didehydro amino acids result in the multiple (five) thioether bridges.

The term "protease" (also called a peptidase or proteinase) indicates any enzyme that performs proteolysis, (begins protein catabolism) by hydrolysis of the peptide bonds that link amino acids together in a polypeptide chain. Proteases can be classified into seven broad groups based on the amino acid at the (protease's) active site used to perform a nucleophilic attack on the substrate: Serine proteases—using a serine alcohol; Cysteine proteases—using a cysteine thiol; Threonine proteases—using a threonine secondary alcohol; Aspartic proteases—using an aspartate carboxylic acid; Glutamic proteases—using a glutamate carboxylic acid; Metalloproteases—using a metal, usually zinc; Asparagine peptide lyases—using an asparagine to perform an elimination reaction (not requiring water), as would be understood by a skilled person. In particular, Aspartic, glutamic and metalloproteases activate a water molecule which performs a nucleophilic attack on the peptide bond to hydrolyse it. Serine, threonine and cysteine proteases use a nucleophilic residue in attack (usually in a catalytic triad). That residue performs a nucleophilic attack to covalently link the protease to the substrate protein, releasing the first half of the product. This covalent acyl-enzyme intermediate is then hydrolyzed by activated water to complete catalysis by releasing the second half of the product and regenerating the free enzyme. Proteases are involved in digesting long protein chains into shorter fragments by splitting the peptide bonds that link amino acid residues. Some detach the terminal amino acids from the protein chain (exopeptidases, such as aminopeptidases, carboxypeptidase A); others attack internal peptide bonds of a protein (endopeptidases, such as trypsin, chymotrypsin, pepsin, papain, elastase). Some proteases can be promiscuous and react with wide range of protein substrates. This is the case for example of digestive enzymes such as trypsin which have to be able to cleave the array of proteins ingested into smaller peptide fragments. Promiscuous proteases typically bind to a single amino acid on the substrate and so only have specificity for that residue. For example, trypsin is specific for the sequences . . . K\ . . . or . . . R\ . . . ('\'=cleavage site). Some proteases are specific and only cleave substrates with a certain sequence or amino acid structure. Proteases, being themselves proteins, can be cleaved by other protease molecules, sometimes of the same variety. This acts as a method of regulation of protease activity. Some proteases are less active after autolysis (e.g. TEV protease) whilst others are more active (e.g. trypsinogen). Specific proteases targeting native membrane substrates are expected to be usable in methods and systems described herein.

In particular specific proteases that target membrane substrates can be compartmentalized with methods herein described. Exemplary specific proteases comprise intramembrane proteases that cleave the transmembrane domain of proteins, such as YaeL from *E. coli* and SpoIVFB from *Bacillus subtilis*, additional proteases described in ([10]). In particular, intramembrane proteases such as YaeL (also called RseP) in *Escherichia coli* play a role in coordinating cell growth and cell division through intramembrane proteolysis of RseA. SpoIVFB is an intramembrane metalloprotease, in *Bacillus subtilis* that cleaves factors required for sporulation (processing of pro-sigma-K to active SigK), Additional proteases such as endopeptidases that target peptidoglycan. The term "endopeptidases" identifies proteolytic peptidases that break peptide bonds of nonterminal amino acids (i.e. within the molecule), in contrast to exopeptidases, which break peptide bonds from end-pieces of terminal amino acids, The relevant peptidase domain can be found by BLAST search on NCBI as will be understood by a skilled person. Additional proteases that target membrane substrates can be identified by a skilled person upon reading of this disclosure.

The term "lysins", also known as endolysins or murein hydrolases, indicates hydrolytic enzymes produced by bacteriophages in order to cleave the host's cell wall during the final stage of the lytic cycle or natively by bacteria themselves in order to remodel their own cell wall. Usually lysins are monomeric proteins with a 25 to 40 kDa range in size. A notable exception is the streptococcal PlyC endolysin, which is 114 kDa and composed of two different gene products, PlyCA and PlyCB, with a ratio of eight PlyCB subunits for each PlyCA in its active conformation as will be understood by a skilled person. Lysins comprise an at least one domain catalyzing the hydrolysis of peptidoglycan and a domain binding to the cell wall substrate. In lysins, the catalytic domain is responsible for the cleavage of peptidoglycan bonds, and can be one of the following five types of lysin catalytic domain: Endo-β-N-acetylglucosaminidase, N-acetylmuramidase (lysozyme-like), Endopeptidase, N-acetylmuramoyl-L-alanine amidase, γ-D-glutaminyl-L-lysine endopeptidase identifiable by a skilled person. In lysins, the cell-binding domain (CBD) binds to a specific substrate found in the host bacterium's cell wall, usually a carbohydrate. In contrast to the catalytic domain, the cell-binding domain is variable, which allows a great specificity and decreases bacterial resistance. Binding affinity to the cell wall substrate tends to be high, possibly so as to sequester onto cell wall fragments any free enzyme, which could compete with phage progeny from infecting adjacent host bacteria. In lysins usually, two or more different catalytic domains are linked to a single cell-binding domain. This is typical in many staphylococcal lysins as well as the streptococcal PlyC holoenzyme, which contains two catalytic domains. Catalytic domains are highly conserved in phage lysins of the same class. In monomeric lysins, the catalytic domain is typically at the N-terminal end of the protein and the cell binding domain is located at the C-terminal end of the protein and the two domains are separated by a short linker region. Target cellular substrate of lysins are peptidoglycans, which consists of cross-linked amino acids and sugars which form alternating amino sugars: N-acetylglucosamine (NAG) and N-acetylmuramic acid (NAM). Endo-β-N-acetylglucosaminidase lysins cleave NAGs while N-acetylmuramidase lysins (lysozyme-like lysins) cleave NAMs. Endopeptidase lysins cleave any of the peptide bonds between amino acids, whereas N-acetylmuramoyl-1-alanine amidase lysins (or simply amidase lysins) hydrolyze the amide bond between the sugar and the amino acid moieties. Finally, the recently discovered γ-d-glutaminyl-1-lysine endopeptidase lysins cleave the gamma bond between D-glutamine and L-lysine residues. Lysins typically target one of the five bonds in peptidoglycan (murein), the main component of bacterial cell walls, which allows the release of progeny virions from the lysed cell in the case of phage lysins and the remodeling of cell wall in the case of native bacterial lysins. These enzymes are being used as antibacterial agents due to their high effectiveness and specificity in comparison with antibiotics, which are susceptible to bacterial resistance.

In some embodiments, lysins that can that can be produced or provided in a cell according to methods and systems of the disclosure and related cell and compositions comprise lysozyme-like lysins, such as Cpl-1 and Cpl-7 that target *S. pneumoniae* peptidoglycan, amidase lysins, such as PlyPSA that targets *L. monocytogenes* peptidoglycan and endopeptidases that target the pentapeptide motif of peptidoglycan, such as Ply500 that targets *L. monocytogenes* peptidoglycan and additional lysins described in reference ([11]).

In particular, the term "lysozyme like lysins" indicates lysins with a catalytic N-acetylmuramidase (lysozyme-like) domain, the term "amidase lysins" identifies with an amidase domain such as amidase 3 domain as shown in the website ncbi.nlm.nih.gov/Structure/cdd/cddsrv.cgi?uid=119407 at the date of filing of the instant disclosure.

In some embodiments herein described, toxic non-native proteins are non-native proteins or peptides that act within the membrane either by direct interaction/disruption of the membrane or through inhibition of membrane biosynthesis proteins. Examples of such toxic non-native proteins include LysE protein from phiX174 bacteriophage and antimicrobial peptides [12]. LysE protein binds to and inhibits the peptidoglycan biosynthesis protein MraY located in the bacterial membrane, thus resulting in cell lysis, and antimicrobial peptides targeting the bacterial cell membrane, and/or targeting other cellular target substrate other than DNA [13].

In some embodiments herein described, the toxic non-native proteins are non-native AMPs lacking of disulfide bonds, such as cecropin, melittin, and adipaecin AMPs In some embodiments described, examples of toxic non-native proteins that can be used in methods and systems of the disclosure and related cells and compositions include LysE and antimicrobial peptides which target membrane substrates, and are harmful to bacterial cells (see Example 2).

In several embodiments, the non-native toxic protein to be produced or provided with methods of the disclosure comprise proteins or peptides that can be used as chemotherapic drugs in treating cancer chemical treatment to kill, inhibit growth or halt the replication and/or spread of cancerous cells in a patient. In some of those embodiments, the non-native toxic protein or peptides are AMPs that can be used in cancer treatment.

In methods and systems herein described and related cell and compositions, one or more toxic non-native proteins are expressed in a cell together with at least one microcompartment protein to form at least one microcompartment comprising the one or more toxic non-native proteins within the cell.

The term "express" as used herein with reference to proteins or peptide indicates the way in which proteins or peptides are synthesized, modified and regulated in living organisms. Typically protein expression includes DNA transcription, RNA processing, translation, and post-translational modification of a protein as will be understood by a skilled person. In particular, the term protein expression refers the process of generating a specific protein within a cell and includes the transcription of the recombinant DNA to messenger RNA (mRNA) and the translation of mRNA into polypeptide chains, which are ultimately folded into functional proteins and may be targeted to specific subcellular or extracellular locations Expression system for protein production comprise a combination of an expression vector, its cloned DNA, and the host cell for the vector that provide a context to allow a non-native gene function in a host cell, that is, produce proteins. Example expression systems are 1) BL21(DE3) host cells that express protein from an expression vector that contains a pT7 phage promoter; and 2) BL21 host cells that express protein from expression vectors that contain pT5 or pRha promoters. Additional expression systems and related host cells, vector and promoters are identifiable by a skilled person The term "cell" as used herein indicates a bacterial cell with bacteria indicating several prokaryotic microbial species which include but are not limited to Gram-positive bacteria, Proteobacteria, Cyanobacteria, Spirochetes and related species, *Planctomyces, Bacteroides, Flavobacteria, Chlamydia*, Green sulfur bacteria, Green non-sulfur bacteria including anaerobic phototrophs, *Radioresistant micrococci* and related species, *Thermotoga* and *Thermosipho thermophiles*. More specifically, the wording "Gram positive bacteria" refers to cocci, nonsporulating rods and sporulating rods, such as, for example, *Actinomyces, Bacillus, Clostridium, Corynebacterium, Erysipelothrix, Lactobacillus, Listeria, Avcobacterium, AMyxococcus, Nocardia, Staphylococcus, Streptococcus* and *Streptomyces*. The term "Proteobacteria" refers to purple photosynthetic and non-photosynthetic gram-negative bacteria, including cocci, nonenteric rods and enteric rods, such as, for example, *Neisseria, Spirillum, Pasteurella. Brucella, Yersinia, Francisella, Haemophilus, Bordetella. Escherichia, Salmonella, Shigella, Klebsiella, Proteus, Pseudomonas, Bacteroides, Acetobacter, Aerobacter, Agrobacterium, Azotobacter, Spirilla, Serratia, Vibrio, Rhizobium, Chlamydia. Rickettsia, Treponema* and *Fusobacterium*. Cyanobacteria, e.g., oxygenic phototrophs.

The term "microcompartment proteins" as used herein indicates proteins that are capable of self-assembling with one with another to form a bacterial microcompartment.

Figure 1B:
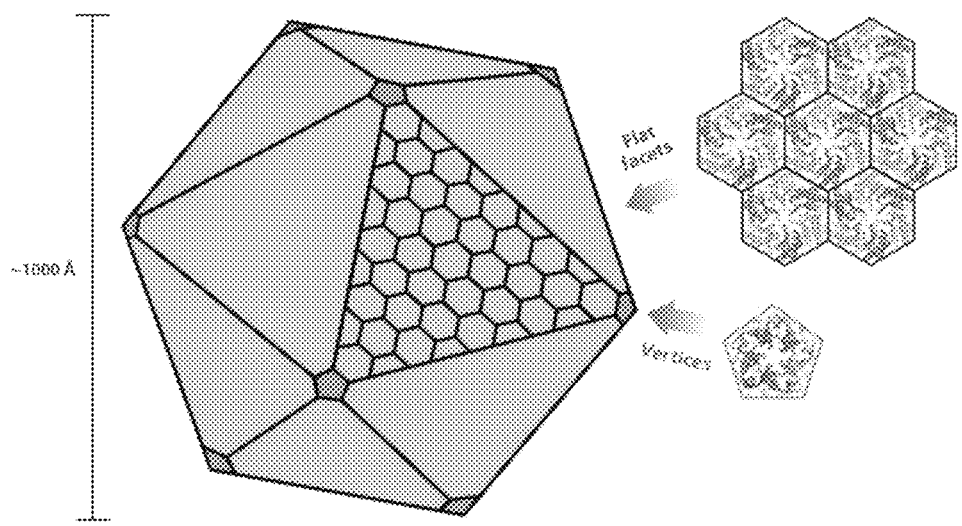

The term bacterial microcompartments (BMCs) refer to organelles that are natively produced by bacteria to organize and sequester enzymes in a biosynthetic pathway within the confines of a protein shell as illustrated in the examples of FIGS. 1A-B. In particular, FIG. 1A shows the transmission electron micrograph of Halothiobacillus neapolitanus cells containing carboxysomes (arrows). FIG. 1B shows a 3D model of a BMC shell. Examples of BMCs in nature include carboxysomes for carbon fixation, in which an increase in the local concentration of a volatile $CO_2$ intermediate is thought to improve reaction efficiency, and propanediol and ethanolamine utilization, in which the BMC shell can prevent the release of cytotoxic aldehyde intermediates, and other bacterial microcompartments as will be recognized by a person skilled in the art.

Figure 2A:
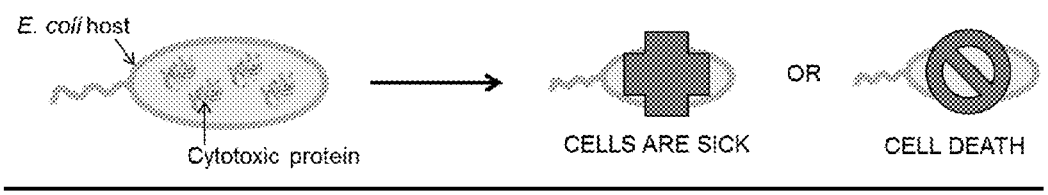
FIG. 2A shows in one embodiment a normal production/expression of cytotoxic proteins in E. coli host.
Figure 2B:
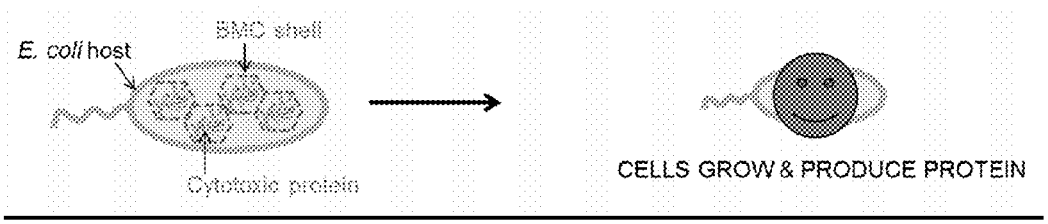
FIG. 2B shows in one embodiment expressions of cytotoxic proteins inside BMCs to prevent toxicity.

In embodiments, herein described cytotoxic proteins are expressed inside BMCs, the BMCs can shield the cells from toxicity of the cytotoxic proteins, allowing the cells to grow and thus produce more cytotoxic proteins as illustrated for example in FIGS. 2A-B.

In some embodiments, methods of the present disclosure comprises introducing into the cell at least one first polynucleotide encoding at least one microcompartment protein, the at least one polynucleotide operatively linked to one or more first regulatory elements leading to the expression of the at least one microcompartment protein in the cell, the at least one microcompartment protein capable of assembling with one or more same and/or different microcompartment proteins to form at least one empty microcompartment within the cell.

As used throughout, "regulatory elements" are regions of non-coding DNA which regulate the transcription of nearby genes. Examples of regulatory elements are promoters and enhancers. Enhancers are regions of DNA that can be bound with proteins (activators) to activate transcription of a gene or transcription. Promoters are regions of DNA that initiate transcription of a particular gene. In the embodiments described, types of promoters used are over-expression promoters, low-level promoters and tunable promoters. Tunable promoters are not constitutive and can be activated or inactivated as a result of culturing conditions and/or additional elements. In some embodiments, tunable promoters are activated in the presence of a compound introduced into the culture media. Examples of tunable promoters include pRha. In the embodiments described, selection of a promoter is determined by several factors including, but not limited to, the nature of the protein being expressed and the desired expression level of the expressed protein. In the embodiments described, low-level promoters are used when the toxic non-native protein is not efficiently localized to the interior of a microcompartment so as to reduce toxicity to a cell from accumulation of the toxic non-native protein in the cell. In the embodiments described, the use of tunable promoters is used to express a protein at a certain level and/or time during culturing of the cell. In the embodiments described, the type of promoter used is influenced by the interplay between the microcompartment proteins and the toxic non-native proteins.

Accordingly, selection of the appropriate regulatory elements the at least one first polynucleotide and for the at least one second polynucleotide can be performed with procedures identifiable by a skilled person.

As used throughout, "operably linked" is defined as a functional linkage between two or more elements. In particular, the term "operably linked" or "operably connected" indicates an operating interconnection between two elements finalized to the expression and translation of a sequence. Functional linkages between elements in the sense of the present disclosure are identifiable by a skilled person. For example, an operable linkage between a polynucleotide of interest and a regulatory sequence (i.e., a promoter) comprises a functional link that allows for expression of the polynucleotide of interest. Another example of operable linkage is provided by a control sequence ligated to a coding sequence in such a way that expression of the coding sequence is achieved under conditions compatible with the control sequences. Operably linked elements are contiguous or non-contiguous and comprise polynucleotides in a same or different reading frame. Additionally, "operably linked" refers to proteins that are linked together wherein the linkage does not impact the function of the individual proteins.

As used throughout, "introducing into the cell" with respect to the polynucleotides refers to inserting a polynucleotide encoding a protein or peptide into a cell or population of cells. One of ordinary skill in the art can readily appreciate that a variety of methods can be used to achieve this such as transformation, transfection, viral transduction and/or injection. In the embodiments described, successful introduction of a polynucleotide into a cell can be assessed by selecting for cells that have taken up the polynucleotide. This is done, for example, by incorporating into the polynucleotide an antibiotic resistance marker against an antibiotic that a cell is typically sensitive to. In some embodiments described, ampicillin resistance genes and kanamycin resistance genes are used on polynucleotides to assess positive insertion of a polynucleotide into a bacterial cell sensitive to ampicillin and kanamycin. Following insertion of a polynucleotide carrying an ampicillin resistance gene, for instance, cells are grown in media containing ampicillin to select for cells that have successfully taken up the polynucleotide.

Introduction of a polynucleotide can be performed for example by chemical transformation or electroporation or other methods identifiable by a skilled person. In some exemplary embodiments performed in *E. coli*, chemical transformation can be performed by incubating $CaCl_2$-treated *E. coli* cells with the plasmid(s) of interest and heat shocking the cells at 42° C. for an appropriate time period (<60 s) to encourage the cells to take up the plasmid(s). Cells are then diluted with rich medium and incubated at 37° C. to allow for heat shock recovery and expression of one or more antibiotic resistance genes. Cells are then plated on solid-agar medium supplemented with the appropriate antibiotic to select for cells that have taken up the polynucleotide. Similarly in electroporation, *E. coli* cells are incubated with the polynucleotide of interest and electroporated at an appropriate voltage to increase cells uptake of the polynucleotide as will be understood by a skilled person. Subsequent steps are the same as for chemical transformation.

In some embodiments introducing into the cell the at least one first polynucleotide can be performed by introducing an expression vector comprising at least one polynucleotide of the at least one first polynucleotide and the one or more first regulatory elements in a configuration leading to transcription of the microcompartment protein carried on the expression vector.

As used throughout, an "expression vector" is a plasmid or virus designed for protein expression in cells. The expression vector is used to introduce a specific gene into a target cell and uses the cell's mechanism for protein synthesis to produce the protein encoded by the gene. In the embodiments described, genes delivered include toxic non-native proteins (such as AMPs and LysE) and microcompartment proteins (such as EutS, M, N, L, and K and PduA, B, J, K, N and U). In the embodiments described, a plasmid is engineered to contain regulatory sequences that act as enhancer and/or promoter regions and lead to efficient transcription of the gene carried on the expression vector. Such plasmids also contain selection markers, such as antibiotic resistance markers, to select for cells that have successfully taken up the plasmid. Examples of plasmids are pMCY 29, pMCY30, pMCY31, pMCY85, pMCY86, pMCY87 and PduP base (see FIG. 3B).

In some embodiments the one or more first regulatory elements s comprise a promoter, and in particular, an over-expression promoter, a low-level constitutive promoter or a tunable promoter. For example in some embodiments, the one or more first regulatory elements can comprise a pRha promoter.

In some embodiments, the one or more first regulatory elements can comprise an enhancer.

In some embodiments, in order to introduce microcompartment proteins to a cell, one or more genes encoding the appropriate microcompartment proteins can be cloned and placed under the control of a promoter (constitutive or inducible) in a given plasmid or other vector of interest containing an antibiotic resistance marker. For BMCs formed by a combination of microcompartment proteins, genes can be placed in tandem behind a given promoter with appropriate ribosomal re-initiation sites to ensure all proteins are expressed. The plasmid containing one or more microcompartment genes is then transformed into the host organism by either chemical transformation or electroporation.

In the case of a constitutive promoter, microcompartment protein is expressed from the plasmid constantly during growth of the host organism. In the case of an inducible promoter, microcompartment protein is expressed from the plasmid by addition of inducer to growth medium (e.g. IPTG, rhamnose). The co-expression of the appropriate microcompartment proteins (e.g., eutS, eutSMNLK, pdu-ABJKNU), results in the formation of empty microcompartments.

In some embodiments, the at least one first polynucleotide comprises one or more polynucleotides encoding for two or more microcompartment proteins.

In some embodiments the at least one first polynucleotide comprises one or more polynucleotides encoding for EutS.

In some embodiments, the at least one first polynucleotide comprises one or more polynucleotides encoding for one or more of PduA, B, J, K, N and U.

In some embodiments, at least one microcompartment proteins can be selected for expression within the cell based on free-energy calculations.

In some embodiments, the BMCs can be redesigned and altered to support functional expression of the cytotoxic non-native proteins to be encapsulated inside. For instance, the BMC expression system can be engineered to over-express the BMC shell proteins to improve BMC yields, thus allowing for higher expression of encapsulated non-native proteins (see Example 1).

In some embodiments, where BMCs is to be overexpressed, expression of one or more appropriate microcompartment proteins can be placed under the control of a highly inducible promoter (e.g., T5, rhamnose). The microcompartment proteins can also be over-expressed from a high copy number plasmid containing an appropriate origin (e.g., pUC) in order to ensure multiple copies of the appropriate genes are expressed. The nucleotide sequence of the microcompartment protein genes can be optimized based on host organism codon usage in order to achieve overexpression as well as according to approaches such as the ones described in reference ([14]) and other approaches identifiable by a skilled person.

In embodiments herein described the methods further include introducing into the cell at least one second polynucleotide encoding for the one or more toxic non-native proteins each operably linked to a leader peptide capable of directing expressed proteins to the at least one empty microcompartment, the at least one second polynucleotide operably linked to one or more second regulatory elements leading to the expression of the at least one toxic non-native protein operably linked to the leader peptide in the cell, In some embodiments introducing into the cell the at least one second polynucleotide encoding for the toxic non-native protein is performed by introducing an expression vector comprising the at least one polynucleotide of the at least one second polynucleotide and the one or more second regulatory elements in a configuration leading to transcription of the toxic non-native protein carried on the expression vector.

In some embodiments, wherein the one or more second regulatory elements comprise a promoter, and in particular an over-expression promoter, a low-level constitutive promoter or a tunable promoter. In some of those embodiments the one or more second regulatory elements comprise a pRha promoter.

In some embodiments, the one or more second regulatory elements comprise an enhancer.

In particular, in embodiments herein described, the introducing of the second polynucleotide is performed in combination with the introducing of the first polynucleotide to obtain the toxic non-native protein within the at least one empty microcompartment within the cell.

For example in some embodiments, a gene for a toxic protein fused to an appropriate BMC targeting tag (PduP, PduD, EutC-tag) can be first be cloned and placed under the control of an inducible promoter that is different from the promoter expressing the microcompartment proteins, in a given plasmid or other vector of interest containing a different antibiotic resistance marker. The plasmid (or other vector) containing the gene for the toxic protein and the plasmid (or other vector) containing one or more genes for the appropriate microcompartment proteins can be co-transformed simultaneously into the same host cell by chemical transformation or electroporation and selected for using the two different antibiotic resistance markers or other markers identifiable by a skilled person. In order to ensure at least partial encapsulation before toxic action, the microcompartment proteins are first expressed by addition of the appropriate inducer, prior to expression of the toxic protein, which would be expressed by the subsequent addition of its respective inducer. For example, in the case of host E. coli expressing microcompartment protein from an IPTG-inducible promoter and toxic protein from a rhamnose-inducible promoter, microcompartment protein can be expressed at the start of growth (early log phase) by addition of IPTG, while toxic protein can be expressed in the middle of growth (late log phase) by addition of rhamnose to ensure at least partial encapsulation before toxic action. The levels of the toxic protein relative to the microcompartment protein can be tuned by varying the inducer concentration to ensure maximum compartmentalization. In particular, the levels of microcompartment protein can be at least 10 fold higher than the levels of toxic protein. Thus, the microcompartment proteins can be expressed at high inducer concentration (e.g. 0.5-1 mM IPTG), while the toxic protein can be expressed at lower inducer concentration (e.g. 0.1-0.2 mM rhamnose). In several embodiments herein described, improved host cell growth and increased production of the toxic protein can be observed under these conditions, compared to cells producing the toxic protein alone.

In some embodiments herein described, two or more polynucleotides can be introduced simultaneously or sequentially. Whether to introduce two or more polynucleotides sequentially or simultaneously depends on the nature of the proteins being expressed from the polynucleotides and the desired results. In the embodiments described, polynucleotides are expressed sequentially, for instance, so as to effectively select for positive insertion of the polynucleotides. For instance, a first polynucleotide encoding for a microcompartment protein and containing an ampicillin resistance gene can be introduced into a group of cells that are sensitive to ampicillin and kanamycin. Following insertion of the first polynucleotide, the cells are cultured in the presence of ampicillin to select for those that have taken up the first polynucleotide. Next, these cells are introduced to a second polynucleotide encoding for a toxic non-native protein and containing a kanamycin resistance gene. Following insertion of the first polynucleotide, the cells are cultured in the presence of kanamycin to select for those that have taken up the second polynucleotide. The resulting cells are thus selected for successful incorporation of both polynucleotides. A similar strategy is taken when the second polynucleotide encodes for a protein that is extremely toxic to the cells and/or inefficiently localized to the interior of a microcompartment. In such an example, a first polynucleotide encoding for a microcompartment protein is introduced before the second polynucleotide encoding for the toxic protein so as to prevent the cell from toxicity following expression of the protein from the second polynucleotide.

In the embodiments described, polynucleotides introduced into a cell encode for a single protein or peptide or several proteins or peptides that function together. Examples of sequences encoding single proteins or peptides include those encoding for the antimicrobial peptides LysE and the microcompartment protein EutS. Examples of sequences encoding for groups of peptides that function together include those encoding for the endolysin PlyC complex (PlyCA and PlyCB) and those encoding for the microcompartment proteins PduA, B, J, K, N and U.

As used throughout, "conditions" for culturing the cells refer to the various elements required to select and/or maintain cells as well as to the various elements required to obtain the desired amount of protein expression from the polynucleotides. Elements required for these purposes include culture media, antibiotics, $CO_2$ concentrations, temperature and additional factors required to ensure that the proteins are expressed; other elements would be readily appreciated by one of ordinary skill in the art. Additionally, elements include factors that are required for the expressed proteins to function as intended (e.g. PlyCA with PlyCB, microcompartment assembly by PduA, B, J, K, N, U). Additionally, elements include factors required for successfully localization of a toxic non-native protein to the inside of a microcompartment.

In the embodiment described, toxic non-native toxic proteins are operably linked to a leader peptide capable of leading the non-native toxic protein to the interior of a microcompartment. The linkage between non-native toxic protein and the leader peptide does not impact the ability of the leader peptide to localize the non-native toxic protein to the interior of the microcompartment. Exemplary BMC leader sequences are PduP, PduD, or EutC-tag as will be understood by a skilled person. For a given toxic proteins suitable leader sequences can be selected and introduced in the construct to target the expression of the non-native toxic protein in the BMCs. Selection of the leader sequence can be performed to provide a tagged construct that is best expressed and targeted to the BMCs of a host cell. In some embodiments, a testing of BMC leader sequence to be fused with the toxic protein can be performed before selection of a leader sequence for a pre-set non-native toxic protein to be produced in a host cell to test possible effects of the leader sequence on toxic protein activity, toxic protein expression (e.g. alteration of the expression level) and/or its BMC targeting ability, by detection methods for each of these activities identifiable by a skilled person. In particular, a construct expressing a non-native toxic protein and a leader sequence can be expressed in a preset host cell and the toxic protein activity, expression and/or targeting ability can be detected. An exemplary procedure to test effects of a leader is provided in Example 4 with reference to PduD leader sequence and the toxic protein LysE. In outcome of the procedure of Example 4 presence of the PduD tag appeared to decrease the total expression of the LysE protein and there was no additional shielding by co-expression of BMC proteins observed. This suggested that the PduD tag itself altered the expression of the protein and that the targeting to the BMCs was not efficient, resulting in no shielding by co-expression of BMCs. Since the regulatory sequences in Example 4 were the same as for Examples 3 and 5, it was possible to conclude that the selection of the BMC tag itself was the reason that the construct of Example 4 showed no additional toxicity shielding by co-expression of BMC proteins.

In some embodiments the at least one leader peptide operably linked to the at least one toxic non-native protein comprises amino acid residues 1-19 of EutC.

In some embodiments the least one leader peptide operably linked to the at least one toxic non-native protein comprises amino acid residues 1-18 of PduP and amino acid residues 1-20 of PduD.

In some embodiments, the leader peptide is selected and linked to the toxic protein in a configuration inactivating the toxic protein. This inactivation will depend on the nature of the toxic protein as well as interaction between the leader sequence and the toxic protein that can be tested by providing the construct with the non-native toxic protein and leader sequence and testing the provided construct to detect native toxic protein activity with procedures identifiable by a skilled person upon reading of the present disclosure. In some of those embodiments, the non-native toxic proteins linked a leader sequence in configuration inactivating the non-native toxic proteins are expected to comprise small toxic proteins, such as AMPs, as fusions of small toxic proteins with other carrier proteins (e.g., GST, thioredoxin) has been shown to inactivate AMPs (see reference [15]).

In the exemplary systems described in the example section, the microcompartment proteins were placed under the control of a T5 IPTG-inducible promoter (pT5) in a high copy number plasmid containing a pUC origin and an ampicillin resistance marker. The toxic protein was placed under the control of a titratable rhamnose inducible promoter (pRha) in a high copy number plasmid containing a pUC origin and a kanamycin resistance marker. To ensure timely sequestration, the microcompartment proteins are expressed first from the pT5 promoter by addition of IPTG at the start of growth (early-log phase). The toxic protein can subsequently be expressed by addition of an appropriate concentration of rhamnose in the middle of growth (mid to late-log phase). The concentration of rhamnose is empirically tuned to determine the correct balance of toxic protein to microcompartment protein to ensure maximum compartmentalization. (The key regulatory elements here are the two different promoters used)

In some embodiments, the present disclosure provides a method to express significant amounts of non-native, cytotoxic proteins in a host organism for isolation and production purposes. The method can be applied to proteins of interest that are difficult to produce due to their cytotoxicity to the host organism. In an exemplary method, cytotoxic, non-native proteins are engineered to be encapsulated in bacterial microcompartments (BMC) in E. coli in order to prevent their cytotoxicity. As proof of this concept, the cytotoxic non-native protein Lysis E (LysE) from bacteriophage phiX174 was targeted to the interior of BMCs in the cytoplasm of E. coli as described in Example 2.

In some embodiments, the present disclosure addresses issues associated with production of non-native, cytotoxic proteins in the host organism E. coli, and can be associated with in vitro purification systems (cell free expression, as described in the www webpage lifetechnologies.com) excretion tags excreting the cytotoxic proteins from E. coli (as described in the www webpage dna20.com), which are used to produce cytotoxic proteins.

In some embodiments, methods and systems of the disclosure herein described can express cytotoxic proteins directly in bacterial microcompartments to minimize toxicity, and/or reduce problems associated with proper folding and secretion associated with secretion tags. The methods, systems and related compositions and cells of the disclosure can result in several embodiments with reduced costs and higher production levels compared to those of prior methods.

An exemplary illustration of steps of methods to provide one or more toxic non-native proteins herein described and in particular LysE are illustrated with reference to exemplary BMC expressed in E. coli cells through use of specific regulatory sequences as will be understood by a skilled person.

First, a fusion gene of the desired toxic protein with an N-terminal BMC targeting tag (such as pduP-tag, pduD-tag, or eutC-tag) and a C-terminal affinity tag for purification (e.g., his$_6$, strepII) is created. Peptidase cleavage sites (e.g., thrombin, factor Xa) is also placed between the BMC targeting tag and toxic protein and the toxic protein and affinity tag to later cleave off the tags if necessary. The fusion gene is placed under the control of an inducible promoter (e.g., pRha) in a plasmid of interest.

A BMC plasmid is created to synthesize empty microcompartments by expression of particular shell proteins (e.g., pduABJKNU, eutSMNLK, or eutS). The expression cassette is then placed under the control of an inducible promoter different from the one used in the fusion gene (e.g., pT5) in a plasmid of interest.

The plasmid containing the desired toxic, non-native protein and the BMC plasmid are co-transformed into an E. coli expression strain (e.g., BL21 cells).

The transformed E. coli cells then grow in an appropriate medium (LB medium) at an appropriate temperature. The cells are first induced for empty microcompartment formation using the inducer for the plasmid containing the microcompartment proteins (e.g., IPTG for the pT5 promoter). Subsequently, the cells are induced for toxic protein production after a desired amount of time using the inducer for the toxic protein plasmid (e.g., rhamnose for the pRha promoter). These conditions will segregate the toxic proteins to the compartments.

In order to isolate the toxic protein of interest inside microcompartments, the cells are harvested after desired induction time and resuspended in an appropriate buffer. The cells are then lysed by an appropriate method including sonication, French press lysis, detergent lysis with lysozyme and other methods identifiable to a person skilled in the art. The cell debris can be removed by centrifugation at 12,000 g, 4° C. for 10 min and supernatant can be collected.

To collect the toxic protein of interest, appropriate detergent is added to the soluble fraction if necessary (e.g., Empigen BB) and incubated for sufficient time to solubilize desired protein. The soluble fraction is then loaded on an affinity chromatography column. The column is washed and the desired protein is eluted with the appropriate buffers. The fractions containing the desired protein can then be collected and stored as necessary.

In some exemplary embodiments, the cytotoxic non-native protein Lysis E (LysE) from bacteriophage phiX174 is targeted to the interior of BMCs in the cytoplasm of E. coli (see Example 2). Encapsulation of the LysE protein in BMCs enhanced growth and production of LysE in E. coli, so that it can be isolated in relatively high amounts. More specifically, in this example, a first polynucleotide encoding for BMC proteins PduA, B, J, K, N, U was introduced to E. coli. These proteins formed a BMC shell within E. coli. A second polynucleotide encoding for the toxic non-native protein LysE coupled to a PduP tag (or leader peptide) is also introduced to these cells. The LysE successfully localize to the interior of the BMC.

Figure 3A:
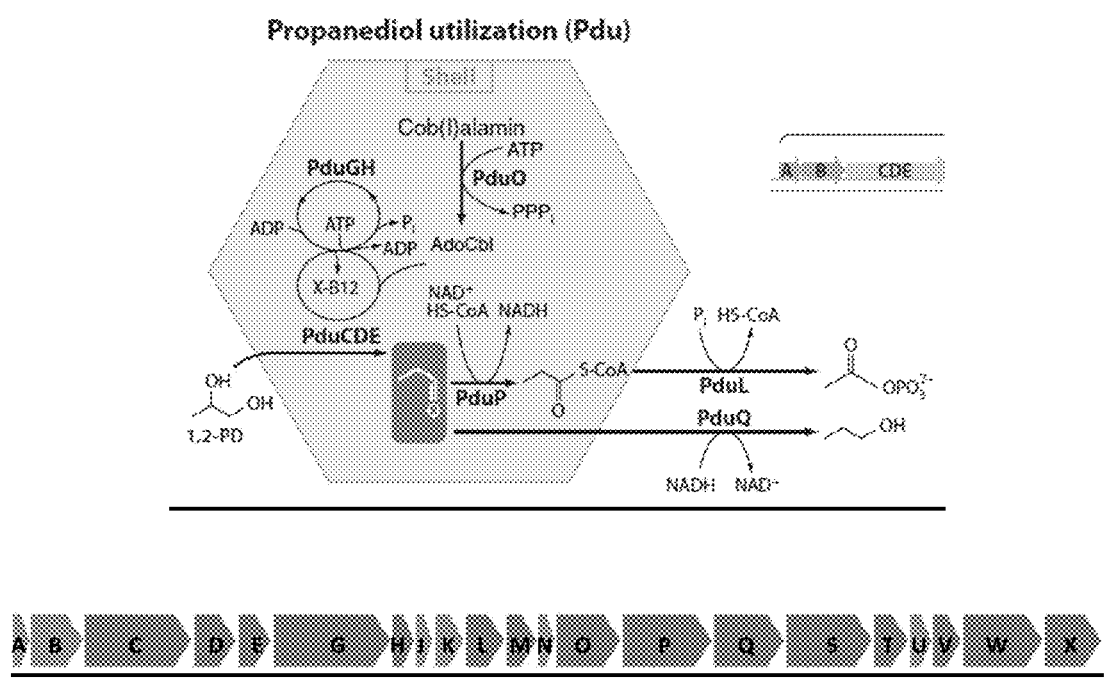
FIG. 3A from reference [1] shows biosynthetic pathway for propanediol utilization (Pdu) and the structure of Pdu operon. Cytotoxic aldehyde intermediate is highlighted.
Figure 3B:
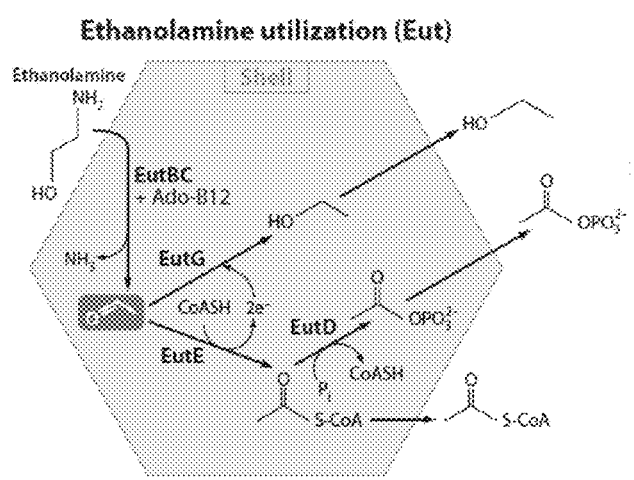
FIG. 3B from reference [1] shows biosynthetic pathway for ethanolamine utilization (Eut) and the structure of eut operon. Cytotoxic aldehyde intermediate is highlighted.
Figure 3B:

In particular, two DNA constructs (or expression vectors) are expressed. The first DNA construct contains genes encoding BMC shell proteins (microcompartment proteins) that comprise an "empty" BMC. Different BMC systems can be used for constructing the BMC encoding genes, for example, the BMC pathway genes for propanediol utilization from *C. freundii* (pducy) and propanediol and ethanolamine utilization from *S. enterica* (pdrs, and eul respectively). FIG. 3A shows biosynthetic pathway for propanediol utilization (Pdu) and the structure of Pdu operon. FIG. 3B shows biosynthetic pathway for ethanolamine utilization (Eut) and the structure of eut operon. Cytotoxic aldehyde intermediate is highlighted. In case of the pdu system (propanediol utilization) (FIG. 3A), there are 6 genes (components A, B, J, K, N, and U) from propanediol utilization in *Salmonella enterica* (pduABJKNU) that have previously been shown to produce "empty" BMCs in *E. coli* (1, 2). In case of the Eut system (ethanolamine utilization) (FIG. 3B), there are 5 genes (components S, M, N, L, and K) from ethanolamine utilization in *S. enterica* required to produce empty BMCs in *E. coli*.

The second DNA construct contains a gene that encodes a non-native cytotoxic protein, such as LysE, fused to 1) an 18 amino acid N-terminal tag (such as PduP tag; leader peptide) that has been previously shown to target non-native proteins to the interior of "empty" BMCs (3) and 2) a purification tag such as C-terminal hexahistindine (His6) tag for standard affinity chromatography protein purification (4). Peptidase cleavage sites such as FactorXa and thrombin are placed between LysE and the PduP tag and between LysE and the His6 tag, respectively, for later cleavage of the tags from LysE if desired (see FIG. 4A and FIG. 4B).

Figure 4A:
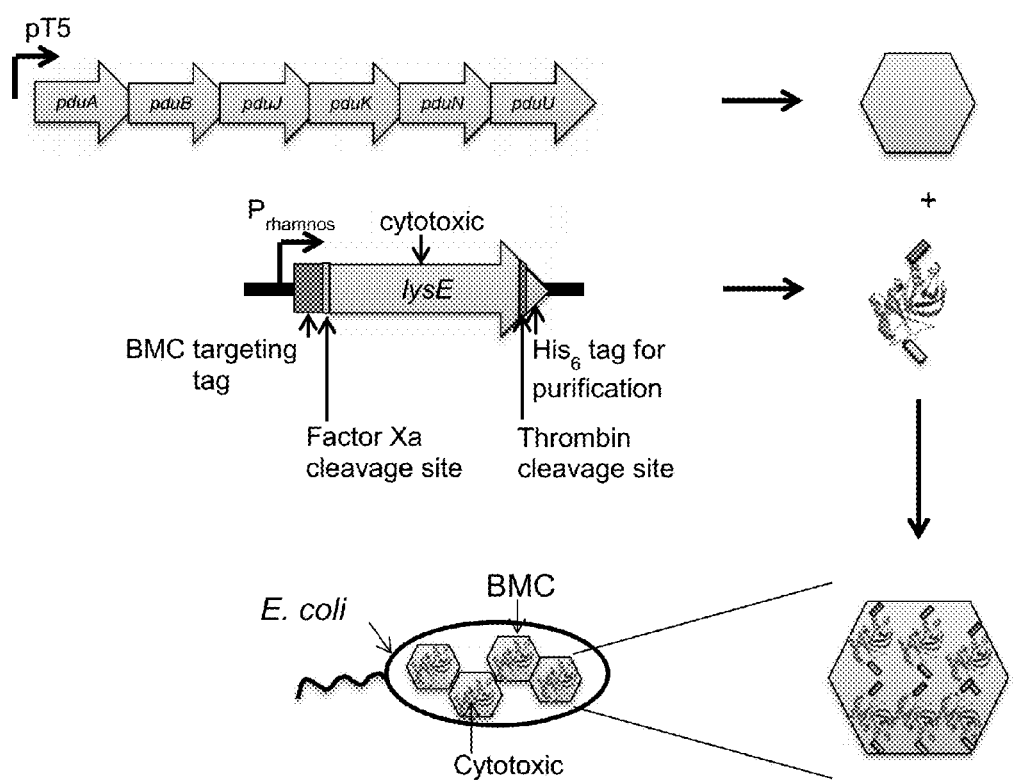
FIG. 4A illustrates in one embodiment the design of a PduP-LysE/pduABJKNU system. The first DNA construct contains the genes necessary to produce empty BMCs. The second DNA construct contains the cytotoxic protein LysE that will be targeted to the interior of BMCs.
Figure 4B:
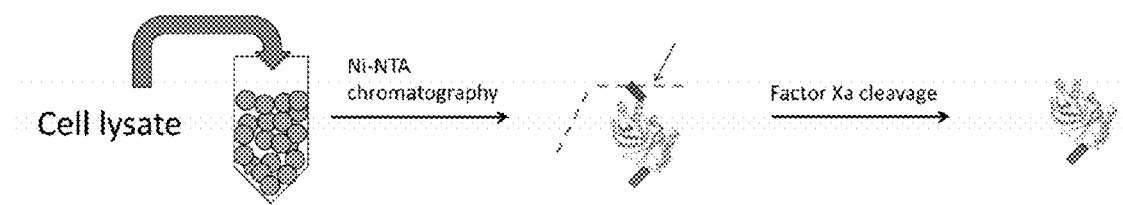
FIG. 4B shows the strategy to purify LysE from cells via Ni-NTA affinity chromatography.

FIG. 4B shows the strategy to purify LysE from cells via Ni-NTA affinity chromatography. Cell lysate from cells co-expressing BMC shell proteins and LysE can be loaded onto a Ni-NTA column and eluted using a high concentration of imidazole. In case there is co-purifying BMC shell protein, the BMC shell protein can be removed by cleaving the BMC targeting tag from the LysE using the protease Factor Xa. Purified LysE can then be purified without contaminating BMC shell protein.

In order to differentially control protein expression from these two DNA constructs, the pduABJKNU genes are placed under the control of an IPTG (isopropyl-1-thiogalactopyranoside) inducible, T5 promoter in a plasmid that confers ampicillin resistance, while the gene fusion for PduP-LysE is placed under the control of a tunable, rhamnose inducible promoter in a plasmid that confers kanamycin resistance (see FIG. 4A).

For expression (production) of PduP-LysE-His6 inside BMCs, protein from both of these DNA constructs can be co-expressed using 0.5 mM IPTG and 0.2 mM rhamnose (agents needed for activation of the tunable promoters). IPTG can be added at the start of growth, while rhamnose is added at mid to late-log phase to ensure that BMC proteins are present for maximum encapsulation of PduP-LysE-His6. If the presence of BMCs indeed shields toxicity of LysE, then co-expression of LysE and BMCs will improve growth (judged by optical density at 600 nm (OD600)), leading to higher protein production levels compared to expression of LysE alone. As shown in Examples 2-3, cells that co-express PduP-LysE with BMCs have twice the growth level and produced ~2 times more PduP-LysE compared to cells that only express PduP-LysE without BMCs.

Figure 4C:
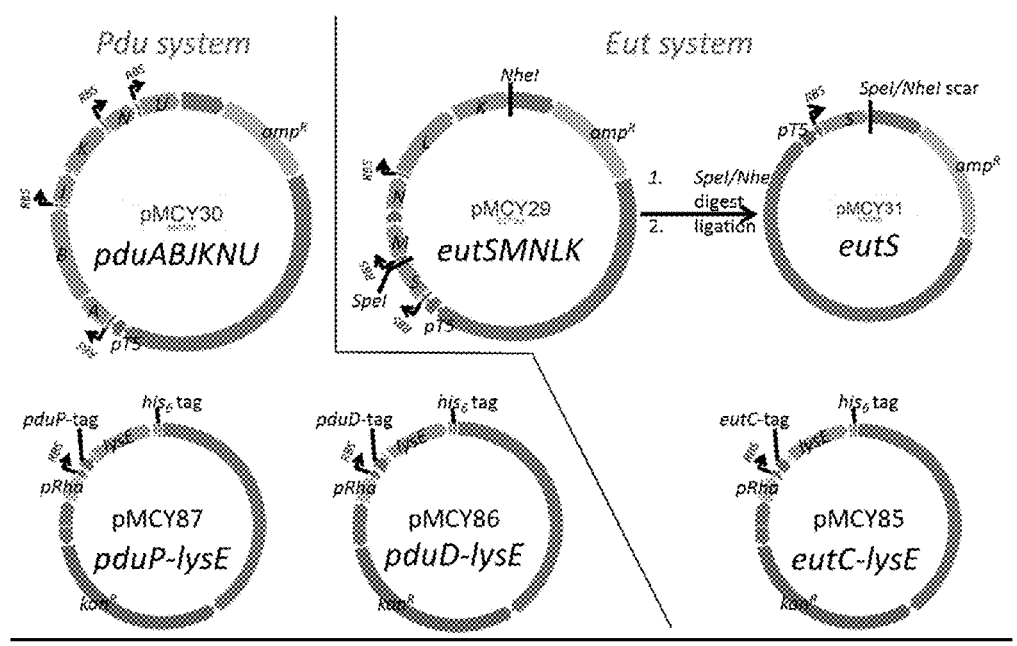
FIG. 4C illustrates different plasmids that have been tested for expression of LysE in BMCs.

In addition to the PduP tag (leader peptide)/pduABJKNU (microcompartment protein) BMC system, a PduD tag (leader peptide)/pduABJKNU (microcompartment protein) BMC system, a EutC tag (leader peptide)/eutSMNLK (microcompartment protein) BMC system from ethanolamine utilization in *S. enterica* (5), a EutC tag (leader peptide) leutS (microcompartment protein) BMC system can also be used to express LysE to obtain an improved yield (FIG. 4C).

Methods, systems and compositions of the present disclosure can be applied broadly to other cytotoxic proteins for expression and purification from bacterial cells by replacing the gene for LysE with the gene for a cytotoxic protein (toxic, non-native protein) of interest and by replacing the medium and regulatory sequences of *E. coli* with the ones of a desired bacteria as will be understood by a skilled person. Thus, the methods, systems, cell and compositions of the disclosure have wide applications in the biosciences, where this novel technology could be used for the efficient production of proteins that are normally difficult to produce.

In embodiments herein described, methods and systems and related cell and composition can be used to produce a toxic non-native protein, by expressing the toxic non-native protein within BMC in a bacterial cell and by isolating the toxic non-native protein from the bacterial cell.

In some embodiments, methods and systems of the disclosure herein described and related cell and composition, can be used to shield the toxicity of pathway intermediates and increase reaction efficiencies in nature. In those embodiments, a toxic non-native protein can be expressed within a BMC and additional molecule forming the pathway can be provided within the cell. In those embodiments, small molecule substrates and products of the enzymes can passively diffuse in and out of the BMCs via pores in the shell proteins, while pathway intermediates remain sequestered inside the BMCs. In such case, not only the toxic pathway intermediates can be shielded from the host organism, but the local concentration of enzymes and substrates also increases, leading to improved reaction efficiency.

The appropriate BMC shell proteins are selected to allow for the transport of molecule substrates and products of the enzymes across the pores of the BMC shell proteins. Such selection can be performed by computational modeling through free-energy calculations in combination with directed sited-mutagenesis. In particular, the energy barriers associated with passage of substrate, enzyme products and intermediate through the pores of the various shell proteins can be computed using established methods [16] as will be recognized by a person skilled in the art. The atomic structures for these computational calculations can be obtained from X-ray crystallography or NMR. Energy barrier calculations can also identify potential sites for directed mutations to the shell proteins in order obtain desired transport properties.

In some embodiments, in order to engineer the compartments to ensure permeability, a crystal structure of desired microcompartment shell proteins is obtained. Examples of the microcompartment crystal structures include those of EutS and EutM from *E. coli* and *C. dficile* and PduA and PduU from *S. enterica* [1]. Next, free-energy calculations are performed on the crystal structure to examine the energy barriers associated with passage of the substrate through the pore of the shell protein using established methods [16]. From the calculated free energy profiles, potential sites can be identified for directed mutations that can be made to the shell proteins to obtain the desired transport properties. Next, mutants of the shell proteins with the identified mutations can be prepared and experimentally or computationally tested for transport properties. The above steps can be repeated as needed until one or more mutated shell proteins with desired transport properties are obtained. The empty microcompartment shell system with the correctly predicted transport properties are expressed in a host organism (e.g., *E. coli*). Tests can be performed using appropriate activity assays to verify whether the substrate can pass through the compartments so that an interior protein can act upon the substrate.

In several embodiments, the present disclosure provides methods and systems that provide in several embodiments a bioengineering application of BMCs that has not been previously explored.

In some embodiments, a cell obtainable by any one of the methods of the disclosure is described, and in particular a cell comprising at least one toxic non-native protein within at least one microcompartment within the cell.

In some embodiments, a cell herein described further comprises various toxic non-native proteins wherein the various non-toxic proteins function and/or aggregate independently of or in combination with one another.

In some embodiments, in cell herein described the various non-toxic proteins reside within the at least one microcompartment within the cell either independently of or in combination with one another.

In some embodiments, in a cell herein described various non-toxic proteins reside within at least two or more microcompartments within a cell.

In some embodiments, in a cell herein described at least one of the microcompartments comprises at least one additional component.

In some embodiments, in a cell herein described the at least one additional component is presented to the at least one toxic-nonnative protein.

In some embodiments, a composition is described comprising one or more cells obtained from any one of the methods of the disclosure, and/or by any one of the systems of the disclosure and/or any one of the cells herein described together with a suitable vehicle.

In some embodiments, the non-native toxic proteins, and related cells herein described are comprised in a composition together with a suitable vehicle. The term "vehicle" as used herein indicates any of various media acting usually as solvents, carriers, binders or diluents for the non-native toxic proteins and/or related cells that are comprised in the composition as an active ingredient. In particular, the composition including the non-native toxic proteins and/or related cells can be used in one of the methods or systems herein described.

As disclosed herein, the non-native toxic proteins, regulatory sequences, vectors and/or related cells herein described can be provided as a part of systems to produce one or more non-native toxic proteins, and in particular can be used in methods to produce or provide a non-native toxic protein herein described. The systems can be provided in the form of kits of parts. In a kit of parts, the non-native toxic proteins, regulatory sequences, vectors and/or related cells and other reagents to produce or provide a non-native toxic protein can be comprised in the kit independently. The non-native toxic proteins, regulatory sequences, vectors and/or related cells can be included in one or more compositions, and each component can be in a composition together with a suitable vehicle.

Exemplary components of a kit of parts and of constructs herein described comprise the nucleotide sequence of the BMC targeting tags, protease cleavage sites, and histidine affinity tags that are codon optimized for maximum expression in *E. coli* such as the one described in the Examples section. Additional components can include labeled molecules and in particular, labeled polynucleotides, labeled antibodies, labels, reference standards, and additional components identifiable by a skilled person upon reading of the present disclosure. The terms "label" and "labeled molecule" as used herein as a component of a complex or molecule referring to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemiluminescence, production of a compound in outcome of an enzymatic reaction and the like.

In particular, the components of the kit can be provided, with suitable instructions and other necessary reagents, in order to perform the methods here described. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

Further details concerning methods and system, cells and compositions of the present disclosure will become more apparent hereinafter from the following detailed disclosure of examples by way of illustration only with reference to an experimental section.

EXAMPLES

The related methods and systems for engineering bacterial systems herein described are further illustrated in the following examples, which are provided by way of illustrating and are not intended to be limiting.

In particular, the following examples illustrate exemplary methods and protocols for over-expressing non-native, cytotoxic proteins or pathways involving these proteins in BMCs for synthetic biology applications. The following examples demonstrate that BMCs are useful platforms to prevent cytotoxicity and to improve efficiency of non-native protein expression. The development of this platform can be broadly used in various fields including biofuels, biopharmaceuticals, biodefense, bioremediation as well as many other applications in bioscience in general. A person skilled in the art will appreciate the applicability and the necessary modifications to adapt the features described in detail in the present section, to additional non-native proteins and bacterial systems and related methods and systems according to embodiments of the present disclosure.

Example 1

Engineering *E. Coli* to Over-Express Empty BMCs for Synthetic Biology Applications Prior to expressing a non-native, cytotoxic protein, an expression system for BMC shell proteins will need to be developed. In this example, methods and systems are described for over-expressing empty BMCs, i.e. BMCs without non-native, cytotoxic proteins inside.

The expression of shell proteins to produce "empty" BMCs in E. coli has been reported using BMC pathway genes for propanediol utilization from C. freundii (pdu$_{Cf}$) and propanediol and ethanolamine utilization from S. enterica (pdu$_{Se}$ and eut respectively) [17-19]. In the case of the eut system, expression of the shell protein EutS is sufficient for formation of empty BMCs, while expression of shell proteins PduA, B, J, K, N, and U are required for the two pdu systems. Expression of all three of these minimal BMC systems are conducted individually in E. coli in order to determine which of these systems is most efficient for expression of cytotoxic proteins.

Using standard molecular biology methods, the genes required for these systems are cloned from the endogenous organisms and inserted into pET expression vectors that can be induced to over-express the proteins.

While over-expression of the pdu$_{Cf}$ system in E. coli has been successfully demonstrated to fill host cells with many empty BMCs [17], over-expression of the pdu$_{Se}$ and eut systems has not yet been demonstrated [18, 19]. Prior studies with the pdu$_{Se}$ and eut systems were only performed using low-copy, constitutive expression systems to express the shell proteins at low levels, yielding only 1-2 BMCs per host cell.

Over-expression of these systems will improve BMC yields and thus allow for higher expression of cytotoxic non-native proteins. The production of homogenous BMCs inside E. coli can be confirmed using transmission electron microscopy (TEM) of both whole cells and purified BMCs as previously described [19].

Minimal BMC shell components required to produce "empty" BMCs are known for propanediol (pdu) and ethanolamine (eut) utilization systems from Salmonella enterica [1,2].

FIG. 3A shows the propanediol utilization (Pdu) pathway and the structure of the pdu operon. FIG. 3B shows the ethanolamine utilization (Eut) pathway and the structure of the ent operon. Components A, B, J, K, N, and U shown in FIG. 3A are the minimal BMC shell components required to produce empty BMCs in the pdu pathway and components S, M, N, L, and K shown in FIG. 3B are the minimal BMC shell components required to produce empty BMCs in the eut pathway.

To over-express empty BMCs, the pET vector containing the appropriate microcompartment genes is first transformed into BL21(DE3) E. coli cells and transformants are selected for using the appropriate antibiotic (e.g., ampicillin). Transformed cells are then grown in LB medium supplemented with the antibiotic at 30° C. Expression of BMC proteins is induced by the addition of 0.5 mM IPTG at mid to late-log phase. Additional growth at 30° C. for 3 h results in the over-expression of the "empty BMC."

Example 2

Engineering E. Coli to Over-Express a Non-Native, Cytotoxic LysE Protein in BMCs: Design of Constructs One of the aspects is to engineer BMCs to encapsulate antimicrobial proteins that are normally cytotoxic to host cells. In this example, methods and systems of over-expressing a non-native, cytotoxic protein lysis protein E (LysE) inside the BMCs are described. LysE protein from bacteriophage (pX174 is expressed inside BMCs and purified in a functional form as a proof of concept that BMCs can be used to shield cytotoxicity of non-native proteins.

Once the expression systems for empty BMCs are established (FIG. 3A), LysE is prepared to target to the interior of the BMCs. It has been demonstrated that non-native proteins can be targeted to the interior of BMCs by "tagging" with the first 18-20 amino acids of PduP and PduD in the pdu systems and EutC in the eut system [18-20]. Table 1 lists the tag sequences for the pdu system and eut system.

TABLE 1

| Tag sequences for the pdu and eut systems | | |
|---|---|---|
| BMC targeting tag | Sequence | SEQ ID NO |
| PduP tag | MNTSELETLIRTILSEQL | 12 |
| PduD tag | MEINEKLLRQIIEDVLRDMK | 13 |
| EutC tag | MDQKQIEEIVRSVMASMGQ | 14 |

LysE can be "tagged" with each of these N-terminal amino acid sequences corresponding to the selected minimal BMC system using standard DNA cloning techniques (see FIG. 4A). In this example, LysE was tagged with PduP tag (BMC targeting tag).

In order to purify LysE, a His$_6$ or StrepII purification tag was placed on the C-terminus of the protein [21] (see FIG. 4A). A factor Xa cleavage site was placed between the BMC tag and LysE so that the BMC shell proteins can be separated from LysE during purification if necessary (see FIG. 4A). The LysE protein can be purified from host cells by affinity chromatography via standard Ni (His$_6$-tag) or Streptactin (Strep-tag) columns (FIG. 4B). FIG. 4C depicts different plasmids that have been tested for expression of a toxic protein LysE in BMCs. Three different empty BMC shell systems (top) were tested in combination with appropriate BMC targeting tag systems (bottom). Systems include pduABJKNU with pduP-lysE, pduABJKNU with pduD-lysE, eutSMNLK with eutC-lysE, and eutS with eutC-lysE. All empty BMC shell system plasmids have an ampicillin resistance marker (amp$^R$) and BMC shell genes are expressed from IPTG inducible T5 promoters (pT5, nucleotide sequence AATTGTGAGCGGATAACAATTAC-GAGCTTC ATGCACAGTGAAATCATGAAAAATTT-ATTTGCTTTGTGAGCGGATAACAATTAT AATATGTGGAATTGTGAGCGCTCACAATTCCACA—SEQ ID NO:5). For the pduABJKNU system, strong ribosome binding sites (RBS, nucleotide sequence TTTAAGGAGGTAAAAA SEQ ID NO:6) were placed prior to pduA, pduJ, pduN, and pcdiU in order to ensure all proteins are expressed; pduAB and pduJK are typically co-expressed and therefore pduB and pduK do not require RBS sites for expression [18]. For the eutSMNLK system, RBS sites were placed prior to eutS, eutM, and eutL; eutN and eutK do not require RBS sites as they are typically co-expressed with eutM and eutL, respectively [19]. All empty BMC shell systems plasmid features were placed in the pD441 vector from DNA2.0, which contains a high copy number origin (pUC). All BMC targeting tag system plasmids have a kanamycin resistance marker (kan$^R$) and the lysE fusion gene is expressed from a rhamnose inducible promoter (pRha, nucleotide sequence CACCACAATTCA-GCAAATTGTGAACATCATCACGTTCATCTTTCCCTG-GTTGC CAATGGCCCATTTTCCTGTCAGTAACGA-GAAGGTCGCGAATTCAGGCGCTTTT TAGACTGG SEQ ID NO:7) with a strong ribosome binding site sequence (AGGAGATATACAT—SEQ ID NO:8) place prior to the start of the lysE fusion gene. The lysE fusion gene encodes the LysE protein with an N-terminal BMC targeting tag and a C-terminal His$_6$ purification tag. The nucleotide sequences for the BMC targeting tag, protease-cleavage sites, and C-terminal His$_6$ purification tag were codon-optimized for expression in *E. coli* and are included below. All BMC targeting tag system plasmid features were placed in the pD861 vector from DNA2.0, which contains a high copy number origin (pUC):

TABLE 2

Codon-optimized nucleotide sequences for the BMC targeting tags, protease cleavage sites, and histidine affinity tags.

| BMC targeting tag | Codon-optimized nucleotide sequence | SEQ ID NO |
|---|---|---|
| EutC-tag | ATGGACCAGAAACAAATTGAAGAAATTGT GCGTAGCGTTATGGCGTCGATGGGTCAGAT CGAGGGTCGT<u>AGATCT</u>*CTGGTCCCGCGTG GCAGC*CACCACCATCATCACCAC | 9 |
| PduD-tag | ATGGAAATCAACGAAAAGCTGCTGCGTCA GATTATTGAAGATGTGTTGCGCGACATGAA AATCGAGGGTCGT<u>AGATCT</u>*CTGGTTCCGC GTGGCAGC*CATCACCACCACCATCAC | 10 |
| PduP-tag | ATGAACACGAGCGAGCTGGAAACCCTGAT CCGTACCATTTTGAGCGAACAGCTGATCGA GGGTCGC<u>AGATCT</u>*CTGGTTCCGCGTGGCTC C*CACCATCACCACCATCAC | 11 |

Bold font = FactorXa site
Underlined = BglII site for insertion of desired toxic protein
Italics = Thrombin site
Bold underlined fonts = His6 tag
Regular font = BMC targeting tag Once these gene constructs were made, appropriate BMC targeting tag systems were co-expressed with a corresponding empty BMC shell system as described in Examples 3, 4, and 5. In order to confirm that the protein is targeted to the BMCs, each construct can also be tagged with green fluorescent protein (GFP) and the cells examined by fluorescence microscopy as previously described [17].

The ability of the BMCs to shield cytotoxicity of LysE from the host organism was tested by monitoring growth of the cells and protein expression levels. If cytotoxicity is shielded, moderate/normal growth of the host organism with relatively high LysE expression levels is expected, compared to poor growth with low expression levels in a control system without co-expression of BMC shell proteins.

Example 3

Figure 5:
FIG. 5 shows the amino acid sequence of an original construct PduP-LysE (SEQ ID NO: 15).

Engineering *E. Coli* to Over-Express a Non-Native, Cytotoxic LysE Protein in BMCs: PduP-LysE+pduABJKNU System In the system tested in this example, BL21 cells were transformed with the following sets of plasmids: 1) pMCY38 (expressing pduP-lysE)+pMCY30 (expressing pduABJKNU) (PduP-LysE+BMCs strain) and 2) pMCY38 only (expressing only pduP-lysE) (PduP-LysE strain). FIG. 5 shows the amino acid sequence of an original construct PduP-LysE. A control strain was also tested in which BL21 cells were transformed with the plasmid pMCY39 (map not shown) from which a non-BMC tagged LysE is expressed (LysE strain). In this control plasmid, the BMC-tag is replaced with a short N-terminal amino acid sequence of MRS.

Figure 6A:
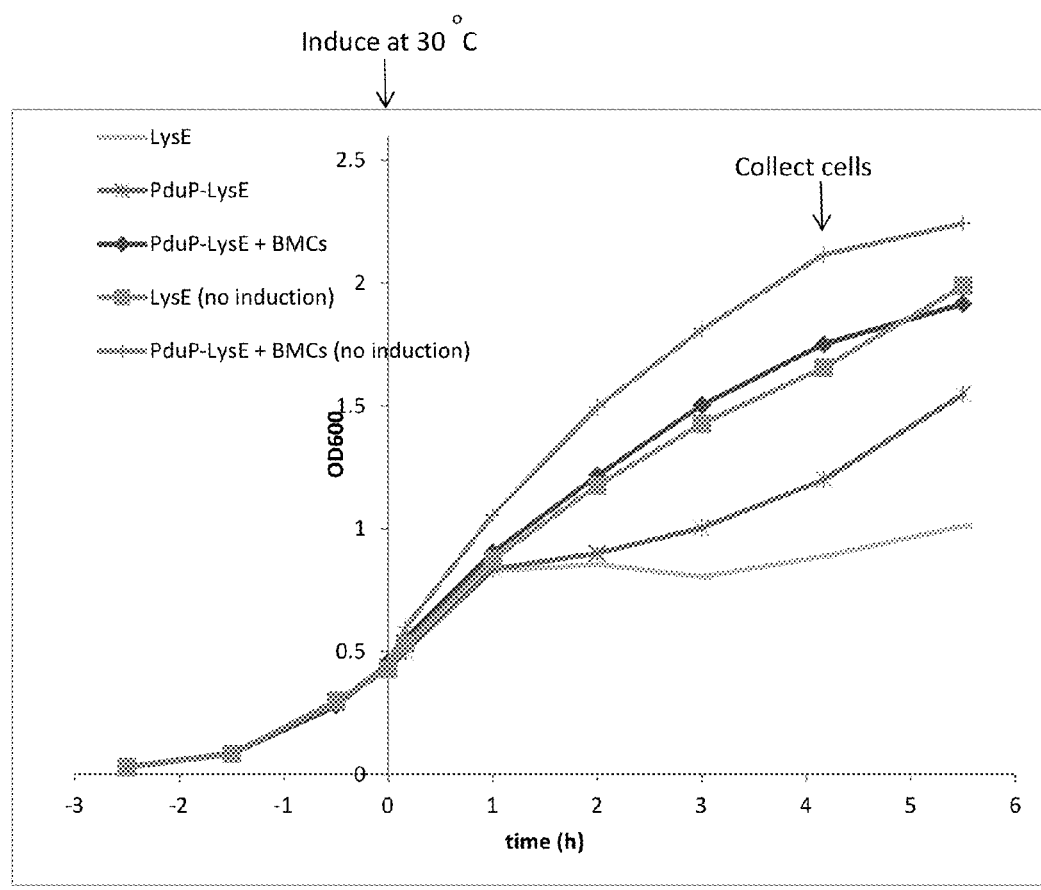
FIG. 6A shows in one embodiment growth curves of the LysE control strain with or without induction, the PduP-LysE strain, and the PduP-LysE+BMCs strain with or without induction.

The transformed cells were grown in LB medium at 30° C. Growth curves are shown in FIG. 6A. Once cells reached an OD600 of ~0.5 (time=0 h), cells were induced with 0.5 mM rhamnose for the LysE control strain and the PduP-LysE strain. Cells were co-induced with 0.5 mM IPTG and 0.5 mM rhamnose for the PduP-LysE+BMCs strain. Control growths were included in which the LysE control and PduP-LysE+BMCs strains were not induced.

Figure 6B:
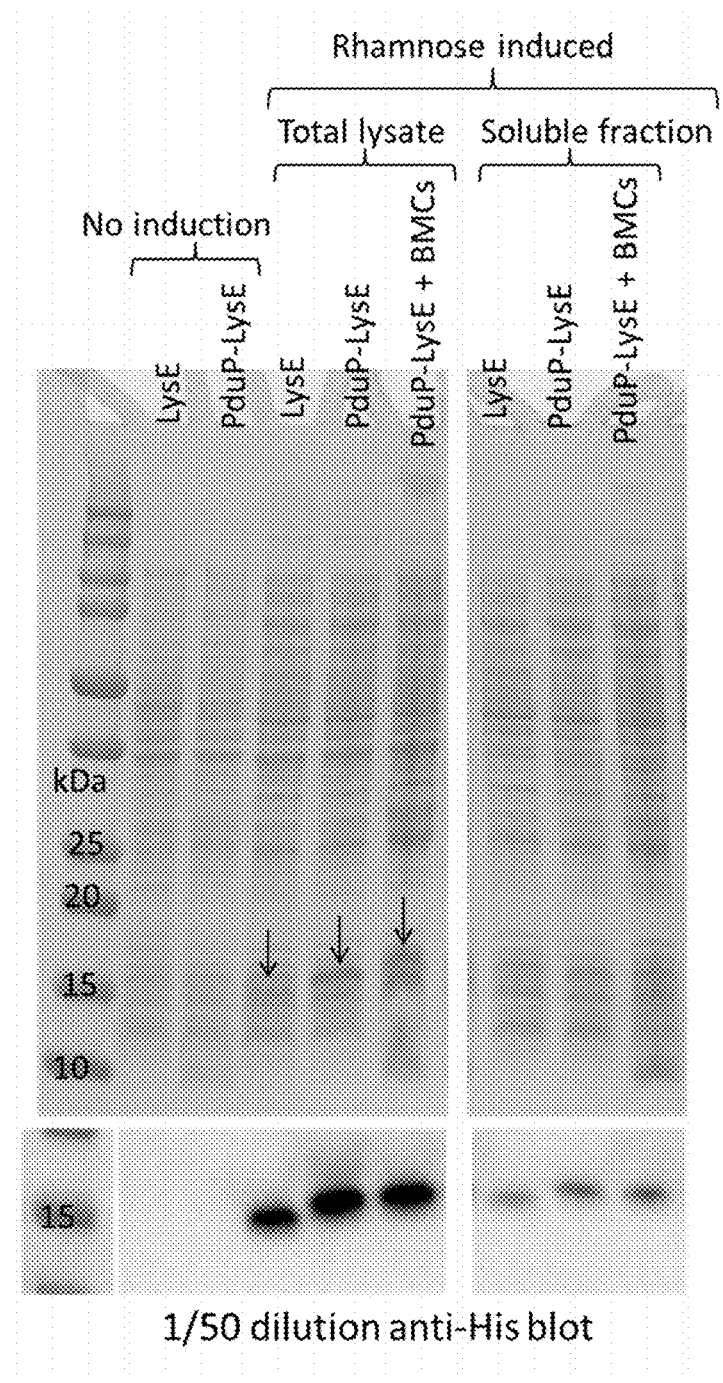
FIG. 6B shows SDS-PAGE and Western blot results.

After 4 h post-induction, cells were harvested and lysed by sonication using standard methods. Total lysate samples were collected after lysis and analyzed by SDS-PAGE and Western blot (FIG. 6B, first 5 sample lanes on the left). For the soluble fraction samples, cell lysates were centrifuged at 20,000 g, 4° C. for 30 min and the supernatant was collected as the soluble fraction. The soluble fraction was subsequently analyzed by SDS-PAGE and Western blot (FIG. 6B, final 3 lanes on the right). Equal amounts of total protein for the total lysate samples were loaded on the SDS-PAGE and Western blot. The same volume of corresponding soluble fraction as the total lysate sample was loaded.

SDS-PAGE gels were stained with standard total Coomassie stain. Arrows denote the position of LysE. For the Western blot (FIG. 6B, bottom panel), an anti-His antibody with reactivity toward the His$_6$ tag on the LysE protein was used to quantify the relative amounts of LysE.

Figure 6C:
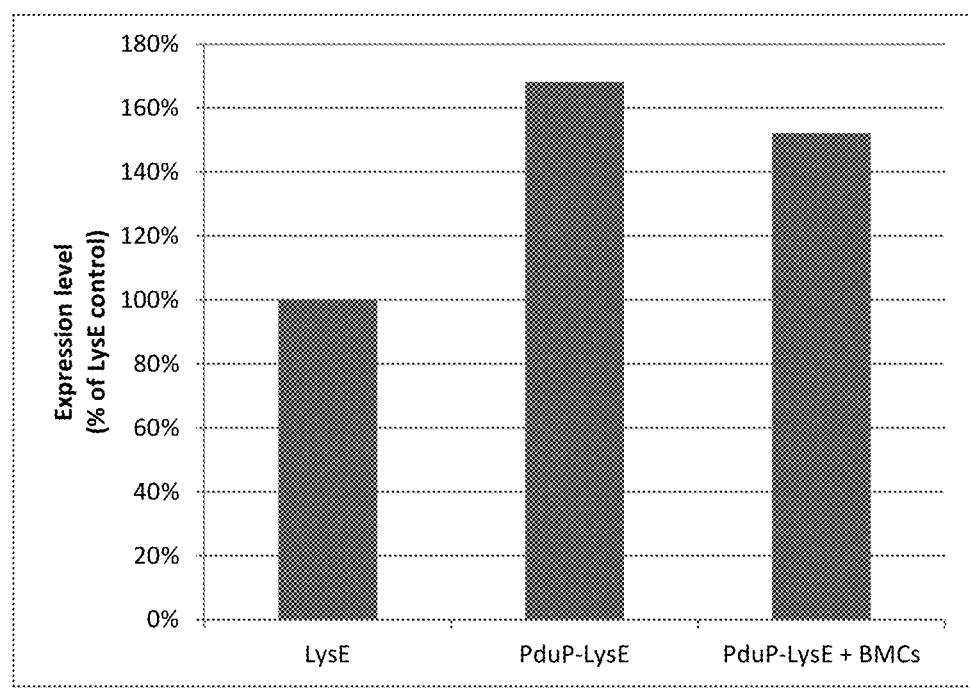
FIG. 6C shows the relative amounts of LysE in the induced strains compared to the induced LysE control strain based on the Western blot intensities.
Figure 6D:
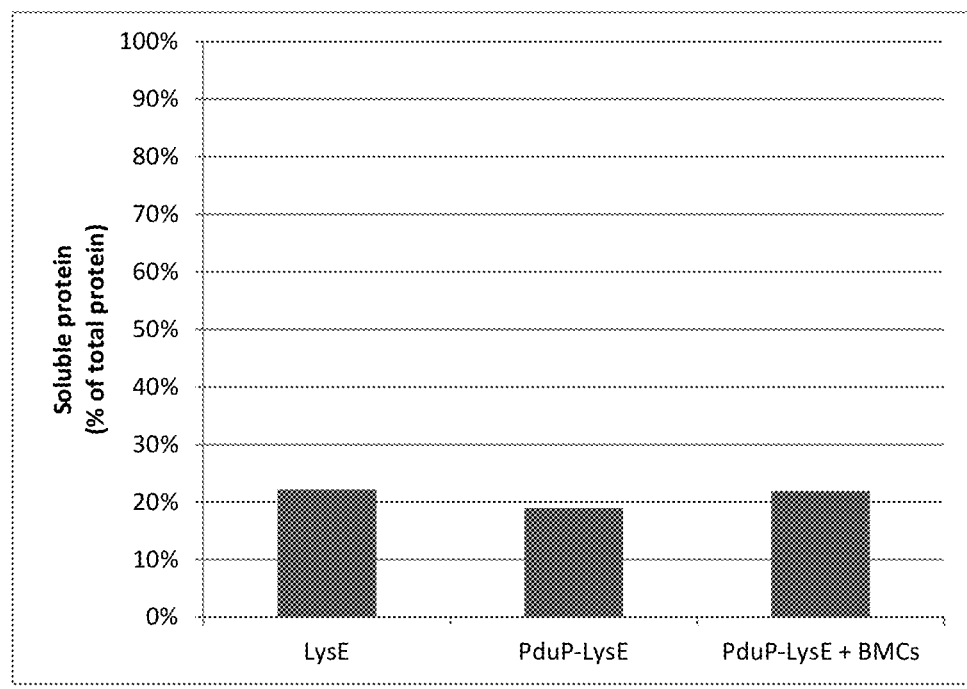
FIG. 6D shows the relative amounts of soluble protein compared to total lysate in each induced strain.

FIG. 6C shows the relative amounts of LysE in the induced strains compared to the induced LysE control strain based on the Western blot intensities. FIG. 6D shows the relative amounts of soluble protein compared to total lysate in each induced strain.

The growth results (FIG. 6A) show that expression of PduP-LysE alone (PduP-LysE strain) had improved growth of host *E. coli* compared to expression of the non-tagged LysE control (LysE control strain). This is primarily due to the lower toxicity of the PduP-LysE construct compared to the LysE control. Co-expression of PduP-LysE and BMCs showed improved growth over the PduP-LysE only strain, suggesting toxicity shielding in the presence of the BMCs.

Western blot results (FIG. 6B) show that both the PduP-LysE strain and the PduP-LysE+BMCs strain produced similar amounts of LysE per cell (given that equal amounts of total protein were loaded in the SDS-PAGE/Western blot analysis), which were ~1.5 times higher than expression of the LysE control. 20% of the total LysE was soluble in all systems.

Example 4

Engineering *E. Coli* to Over-Express a Non-Native, Cytotoxic LysE Protein in BMCs: PduD-LysE+pduABJKNU System In this system, BL21 cells were transformed with the following sets of plasmids: 1) pMCY37 (expressing pduD-lysE)+pMCY30 (expressing pduABJKNU) (PduD-LysE+BMCs strain; and pMCY37 only (expressing only pduD-lysE) (PduD-LysE strain). A control strain was tested in which BL21 cells were transformed with the plasmid pMCY39 from which a non-BMC tagged LysE is expressed (LysE strain). The same experimental procedure described in Example 3 was carried out in this example.

Figure 7A:
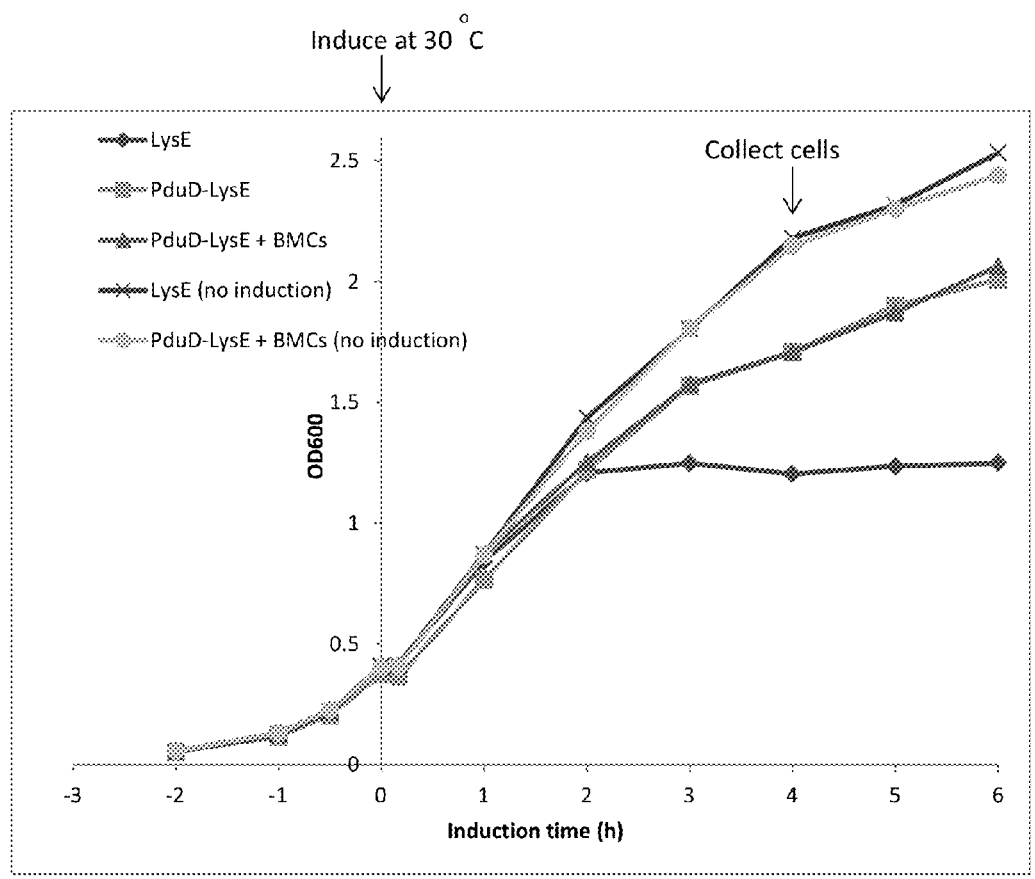
FIG. 7A shows in one embodiment growth curves of the LysE control strain with or without induction, the PduD-LysE strain, and the PduD-LysE+BMCs strain with or without induction.
Figure 7B:
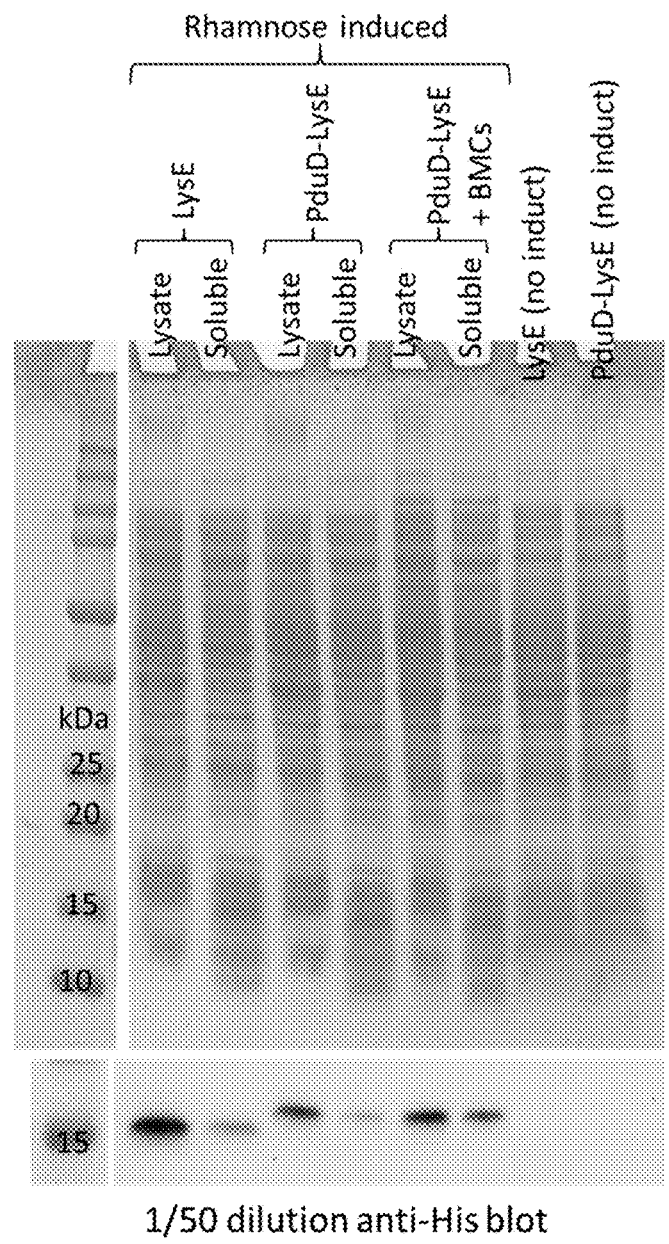
FIG. 7B shows SDS-PAGE and Western blot results.
Figure 7C:
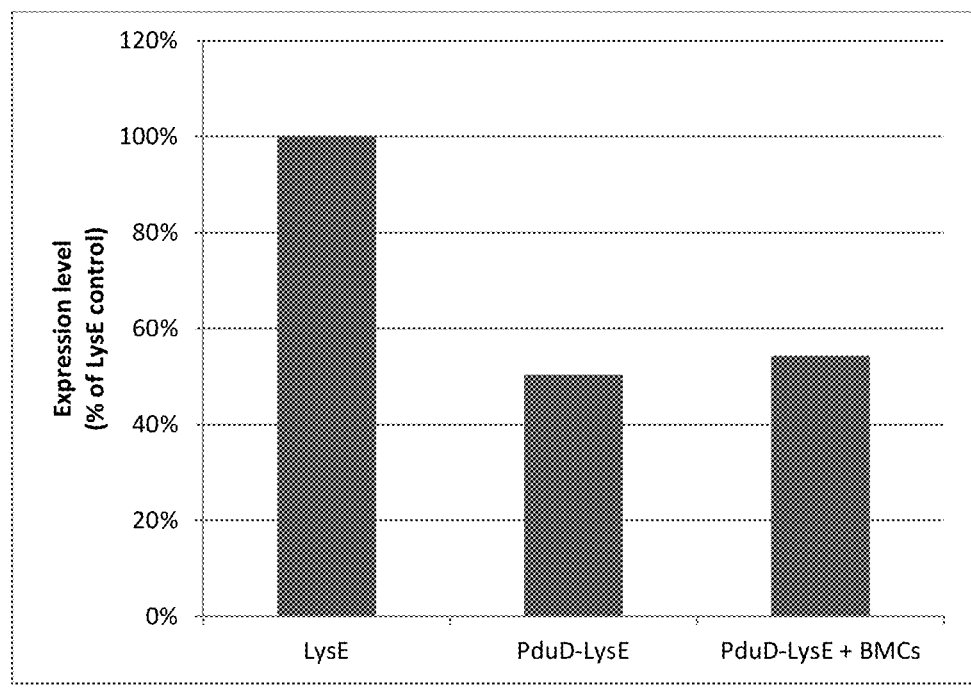
FIG. 7C shows the relative amounts of LysE in the induced strains compared to the induced LysE control strain based on the Western blot intensities.
Figure 7D:
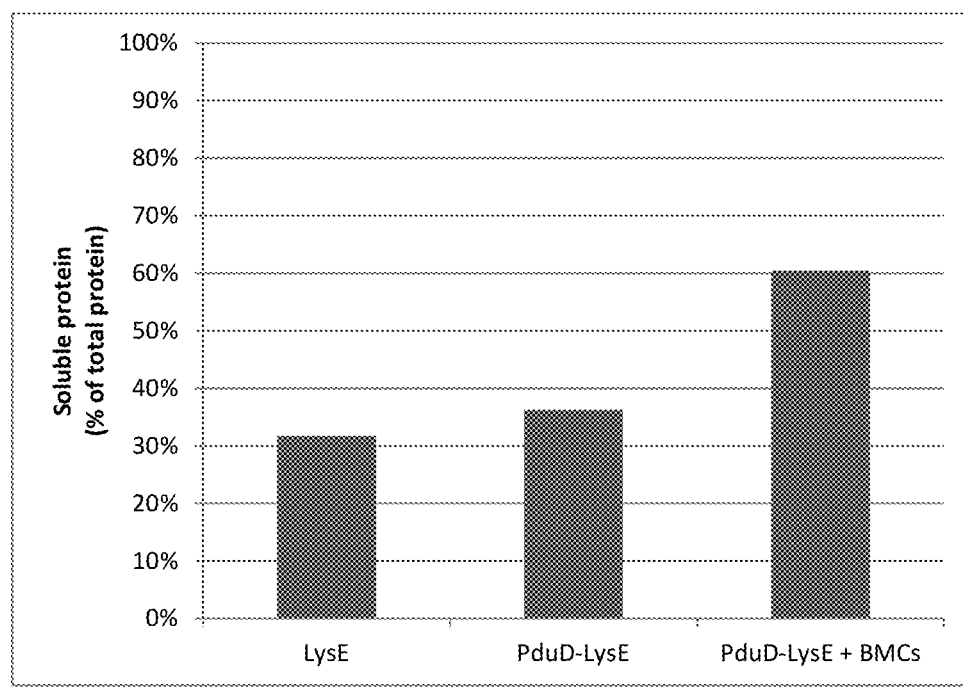
FIG. 7D shows the relative amounts of soluble protein compared to total lysate in each induced strain.

The growth results (FIG. 7A) show that expression of both PduD-LysE and PduD-LysE+BMCs had improved growth over the non-BMC tagged LysE control strain, indicating that the BMCs did not have an added toxicity shielding benefit in this system for LysE. Western blots (FIG. 7B) showed that both strains actually produced less LysE compared to the control strain (~50% of the control strain), which likely accounts for the improved growth in this system.

The presence of the BMCs, however, did appear to improve the solubility of the PduD-LysE based on Western blot (60% versus 30% in the PduD-LysE only strain), although only 1 replicate was performed and it may be within error of the Western blot.

Therefore it appears that the interaction between LysE and the PduD tag affects its expression level (possibly by altering its activity) as well as its ability to target to the BMCs.

Example 5

Engineering *E Coli* to Over-Express a Non-Native, Cytotoxic LysE Protein in BMCs: EutC-LysE+eutSMNLK or eutS System In this system, BL21 cells were transformed with the following sets of plasmids: 1) pMCY36 (expressing eutC-lysE)+pMCY29 (expressing eutSMNLK) (EutC-LysE+eutSMNLK strain); 2) pMCY36 (expressing eutC-lysE)+pMCY31 (expressing eutS) (EutC-LysE+eutS strain); and 3) pMCY36 only (expressing only eutC-lysE) (EutC-LysE strain). A control strain was also tested in which BL21 cells were transformed with the plasmid pMCY39 from which a non-BMC tagged LysE is expressed (LysE strain). The same experimental procedure described in Example 3 was carried out in this example.

Figure 8A:
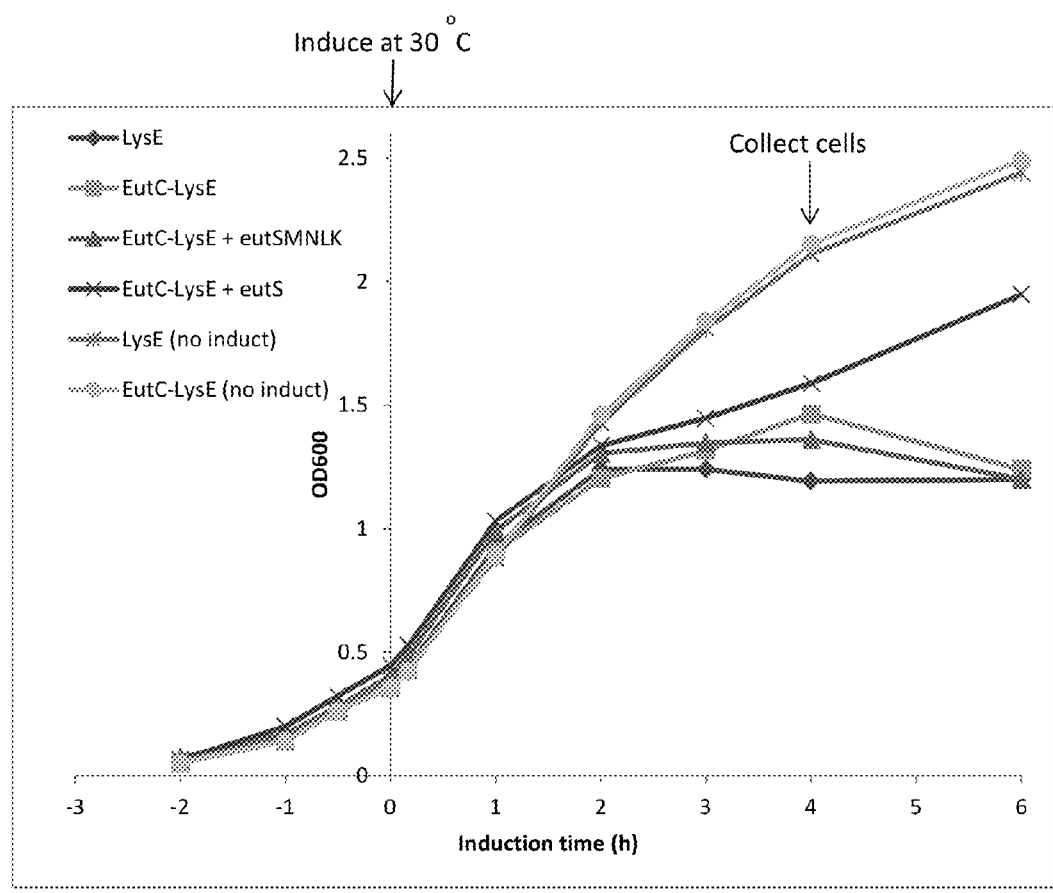
FIG. 8A shows in one embodiment growth curves of the LysE control strain with or without induction, the EutC-LysE strain with or without induction, the EutC-LysE+eutSMNLK strain and EutC-LysE+eutS strain.
Figure 8B:
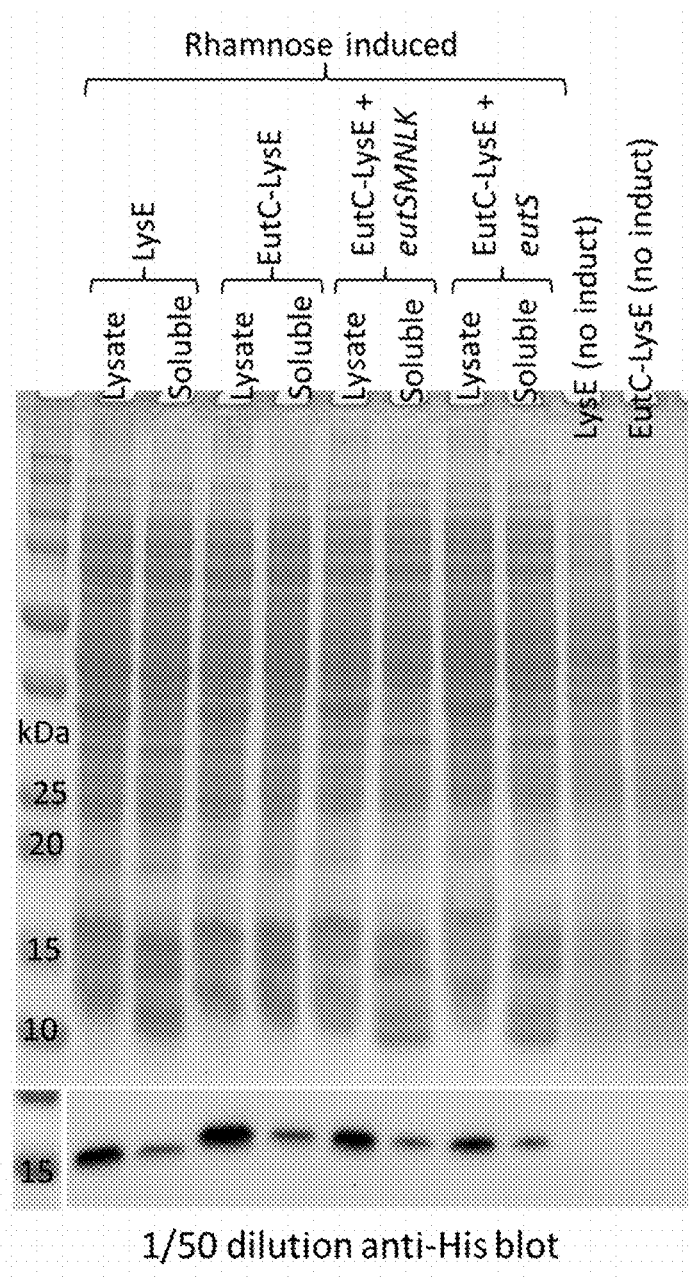
FIG. 8B shows SDS-PAGE and Western blot results in this embodiment.
Figure 8C:
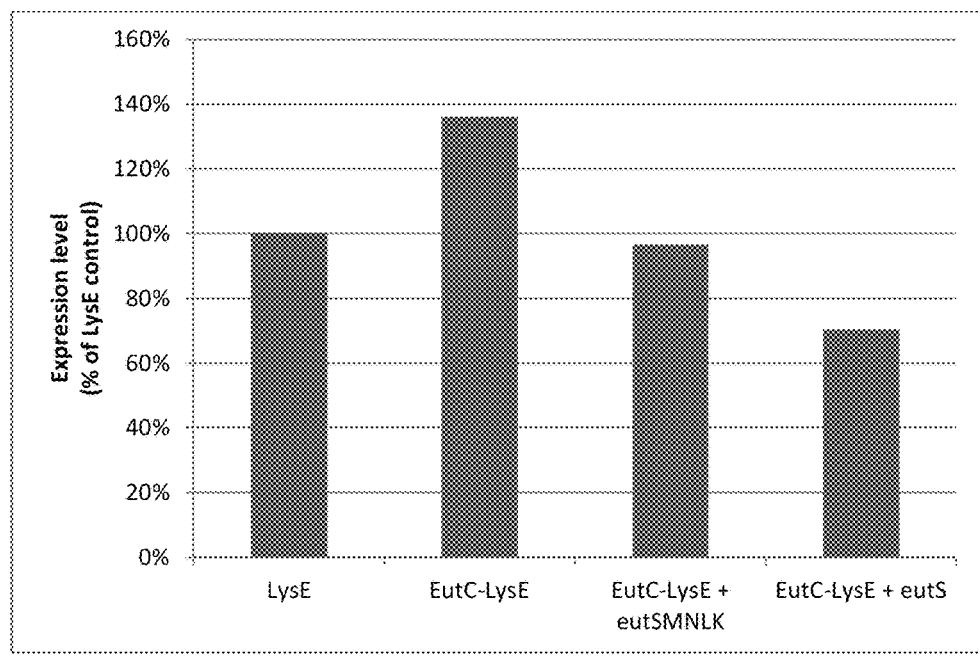
FIG. 8C shows the relative amounts of LysE in the induced strains compared to the induced LysE control strain based on the Western blot intensities.
Figure 8D:
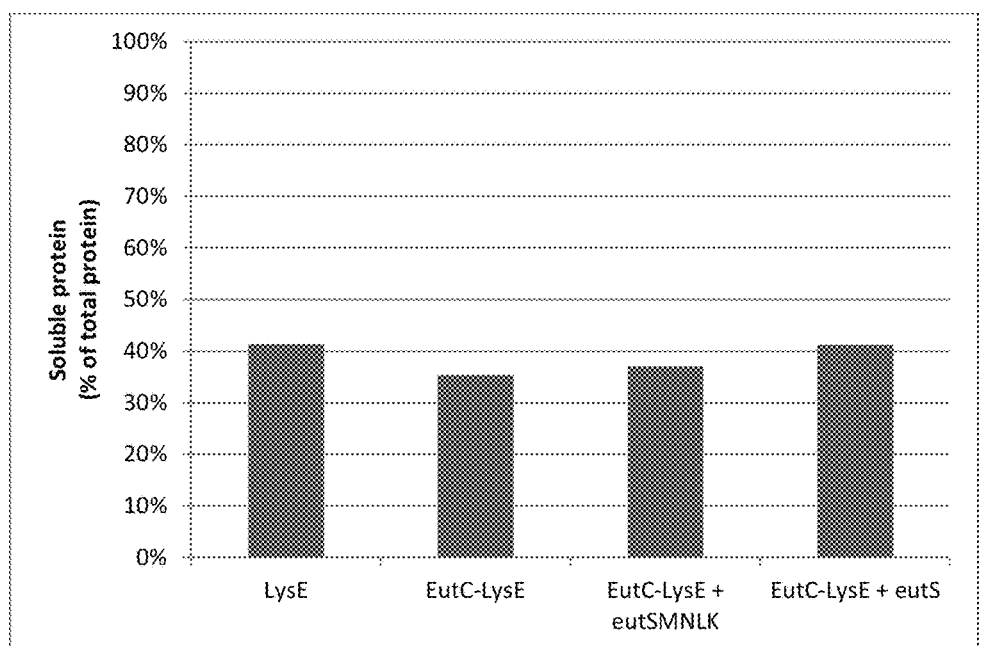
FIG. 8D shows the relative amounts of soluble protein compared to total lysate in each induced strain.

The growth results (FIG. 8A) show that only the EutC-LysE+eutS strain showed improved growth compared to the LysE control strain. However, this strain had only ~70% of levels of LysE in the control strain based on Western blot (FIG. 8B), which may account for the improved growth, suggesting limited toxicity shielding due to the presence of eutS. The expression of EutC-LysE only was higher than the LysE control system, but co-expression of EutC-LysE+eutSMNLK was similar to the LysE control system (FIG. 8C). ~30-40% of the total LysE was soluble in all systems based on Western blot (FIG. 8D).

Example 6

Engineering *E. Coli* to Over-Express a Non-Native, Cytotoxic LysE Protein in BMCs—Localization of PduP-LysE-mCherry A plasmid variation of pMCY38 (pMCY38mch) was created in which a mcherry gene was placed between the lysE gene and the his$_6$ tag gene sequence in order to express a PduP-LysE-mCherry fusion protein. A control plasmid variation of pMCY39 (pMCY39mch) was also created in which a mcherry gene was placed in the same location in order to express a LysE-mCherry fusion protein. BL21 cells were then transformed with the following sets of plasmids: 1) pMCY39mch (expressing lysE-mcherry) (LysE-mCherry strain); 2) pMCY38mch only (expressing only pduP-lysE-mcherry) (PduP-LysE-mCherry strain); and 3) pMCY38mch (expressing pduP-lysE-mcherry)+pMCY30 (expressing pduABJKNU) (PduP-LysE-mCherry+pduABJKNU strain).

Figure 9:
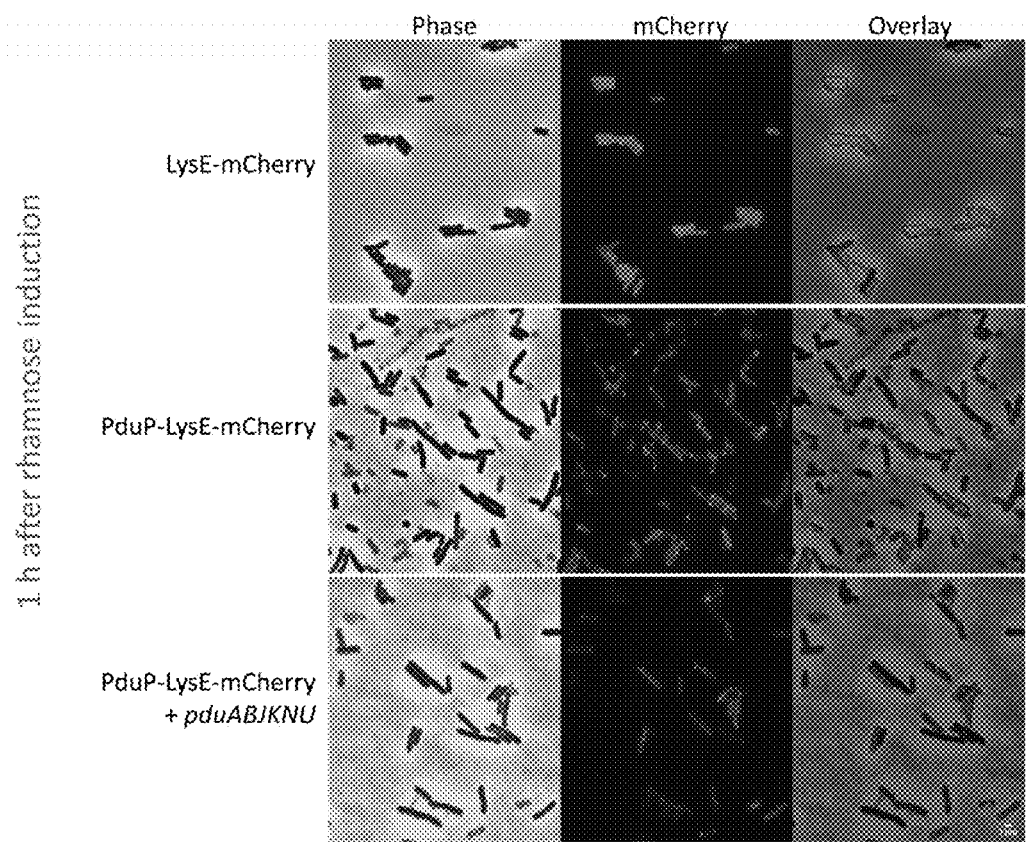
FIG. 9 shows in one embodiment fluorescence microscopy images of cell growth on an agar-pad for the LysE-mCherry control strain, the PduP-LysE-mCherry strain, and the PduP-LysE-mCherry+pduABJKNU strain

Transformed cells were grown in LB medium at 30° C. Once cells reached an OD600 of ~0.5, cells were induced with 0.5 mM rhamnose for the LysE-mCherry control strain and the PduP-LysE-mCherry strain (FIG. 9, top two panels). Cells were co-induced with 0.5 mM IPTG and 0.5 mM rhamnose for the PduP-LysE-mCherry+pduARIKNU strain. At 1 h post-induction, cells were spotted on an agar-pad and imaged by fluorescence microscopy using a 100× phase objective. Images in the left panel (FIG. 9) are phase images showing the outline of the cells, images in the middle panel are the red channel showing mCherry fluorescence, and images in the right panel are overlay images of phase and the red channel.

Results show that PduP-LysE-mCherry has punctate localization both in the presence and absence of pduAB-JKNU, indicating that this protein naturally has punctate localization. The LysE-mCherry has more diffuse localization, but some punctate spots can still be observed. The higher diffuse localization may be due to high mCherry expression levels in this strain after 1 h, as observed by the higher fluorescence intensities observed for the LysE-mCherry strain. Co-localization studies of BMCs with PduP-LysE-mCherry will need to be performed in the future.

Example 7

Engineering *E. Coli* to Over-Express a More Toxic LysE Protein in BMCs

Figure 10:
FIG. 10 shows the amino acid sequence of a PduP-LysE construct with higher toxicity (SEQ ID NO: 16).

The same experimental procedure described in Examples 2-3 was carried out in this example, except that a PduP-LysE construct with a higher toxicity compared to the original one (FIG. 5) was used. The amino acid sequence of the more toxic PduP-LysE construct is shown in FIG. 10, in which arginine and serine shown in FIG. 5 (R and S, bold and underlined in FIG. 5) are deleted.

Figure 11A:
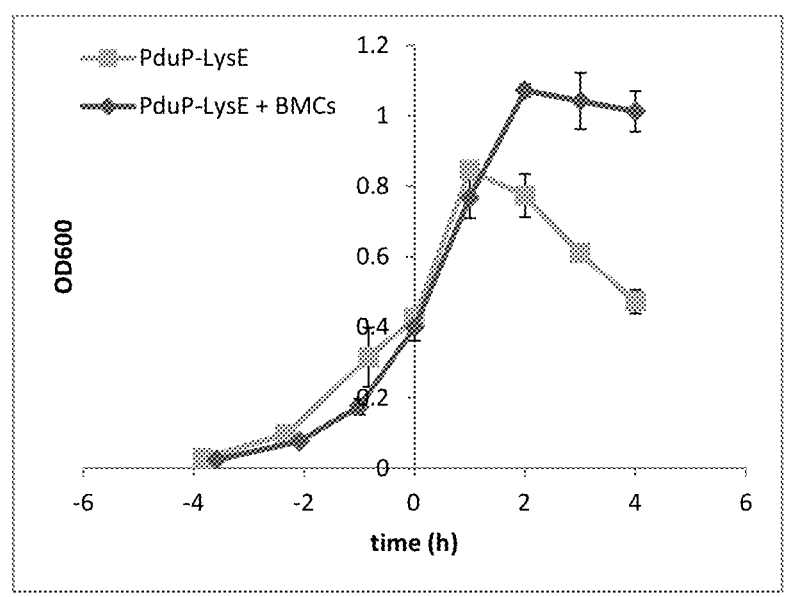
FIG. 11A shows in one embodiment a comparison of growth between cells co-expressing BMCs and PduP-LysE (squares) and cell expressing only PduP-LysE (diamonds).
Figure 11B:
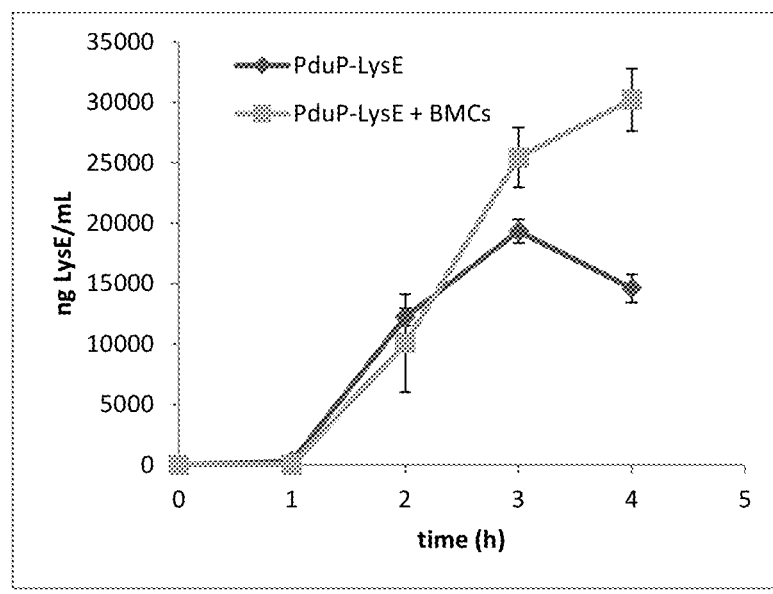
FIG. 11B shows a comparison of PduP-LysE production levels between cells co-expressing BMCs and PduP-LysE (squares) and cell expressing only PduP-LysE (diamonds). Growth was measured by optical density at 600 nm (OD600), while PduP-LysE production levels were measured by Western blots. Toxic PduP-LysE was induced at time 0, while BMC proteins were induced at the start of growth (time=−4 h). Error bars represent 3 biological replicates.

FIG. 11A shows comparison of growth between cells co-expressing BMCs and PduP-LysE (squares) and cell expressing only PduP-LysE (diamonds). FIG. 11B shows comparison of PduP-LysE production levels between cells co-expressing BMCs and PduP-LysE (squares) and cell expressing only PduP-LysE (diamonds). Growth was measured by optical density at 600 nm (OD600), while PduP-LysE production levels were measured by Western blots. Toxic PduP-LysE was induced at time 0, while BMC proteins were induced at the start of growth (time=−4 h). Error bars represent 3 biological replicates.

In particular, plasmids pMCY87 and pMCY30 from FIG. 4C were transformed into *E. coli* BL21 cells in order to co-express PduP-LysE and pdu BMCs, respectively (squares). Only plasmid pMCY87 was transformed into *E. coli* BL21 cells in order to express only PduP-LysE (diamonds). Cells were grown in LB medium. In the case of co-expressing cells, cells were induced at the start of growth (time=−4 h) with 0.5 mM IPTG in order to induce expression of the pxih BMCs. Once cells reached an optical density at 600 nm (OD600) of 0.4 (time=0 h), cells were induced with 0.2 mM rhamnose in order to induce expression of the PduP-LysE. At 0, 1, 2, 3, and 4 h post-rhamnose induction, cells were collected to determine the amount of PduP-LysE present based on quantitative Western blots against a purified standard. Total amounts of PduP-LysE in the cultures were determined (FIG. 11B). The data shows that co-expression of BMCs and PduP-LysE resulted in ~2-fold improvements in both host bacterial growth (FIG. 11A) and PduP-LysE production levels (FIG. 11B), compared to cells expressing only PduP-LysE. The data also shows improved results compared to the one obtained from Example 3.

Figure 12:
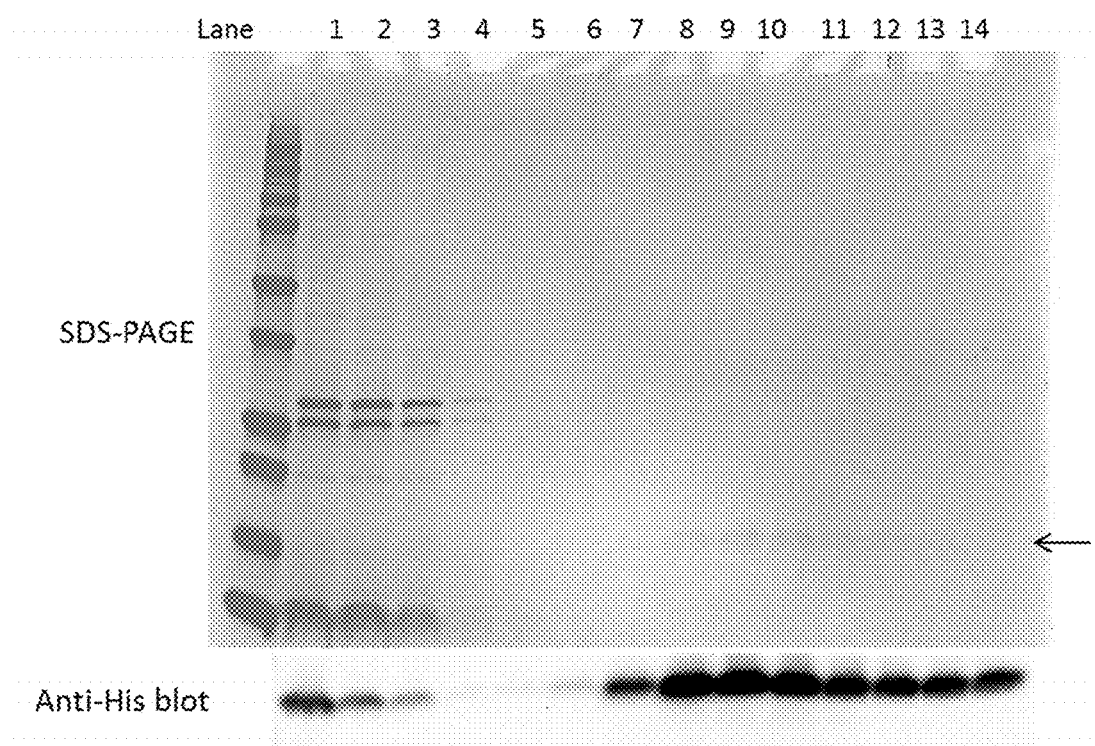
FIG. 12 shows purification of PduP-LysE from isolated BMCs. SDS-PAGE (top) and Western blot (bottom) results show that PduP-LysE can be purified from isolated BMCs by chromatography on a Ni-NTA column in presence of the mild detergent, Empigen BB. Lane 1, isolated BMCs; Lane 2, flow through; Lane 3-5, wash fractions; Lane 6-14, elute fractions with purified PduP-LysE. Arrow denotes PduP-LysE on SDS-PAGE.

FIG. 12 shows purification of PduP-LysE from isolated BMCs. SDS-PAGE (top) and Western blot (bottom) results show that PduP-LysE can be purified from isolated BMCs by chromatography on a Ni-NTA column in presence of the mild detergent, Empigen BB. Lane 1, isolated BMCs; Lane 2, flow through; Lane 3-5, wash fractions; Lane 6-14, elute fractions with purified PduP-LysE. Arrow denotes PduP-LysE on SDS-PAGE.

In this experiment, BMCs were isolated from cells that were co-expressing PduP-LysE and BMCs (at 3 h post-rhamnose induction) using previously described differential centrifugation methods [22]. Isolated BMCs were incubated in 2% Empigen BB (EBB) for 2 h, diluted to 0.4% EBB, and then loaded onto a Ni-NTA column. The resin was washed with 16 column volumes (collected in 8 fractions) of 20 mM imidazole, 0.06% EBB in Tris buffer (100 mM Tris, pH 8.0, 100 mM NaCl). LysE was eluted with 7 column volumes (collected in 10 fractions) of 200 mM imidazole, 0.06% EBB in Tris buffer. The original isolated BMCs, flow through from the column, wash fractions, and elute fractions were analyzed by SDS-PAGE and Western blot (FIG. 2). Results show that PduP-LysE can be purified from isolated BMCs in high purity without contamination of BMC proteins in the presence of the mild detergent EBB.

Example 8

Engineering *E. Coli* to Over-Express CistronA and RegB

The gene for Cistron A could not be cloned into the BMC targeting plasmids described in Example 2 and could not be successfully transformed into BL21 expression cells. This is because, even low basal levels of the Cistron A protein resulted in enough toxicity that the cells cannot maintain the plasmid containing the Cistron A gene. Co-transformation of candidate plasmids containing the Cistron A gene with empty BMC microcompartment plasmids also did not result in the formation of colonies containing plasmid with the Cistron A gene. Thus, it was established that the presence of BMC microcompartment protein was not capable to shield toxicity of the Cistron A gene. Similar results were found for RegB.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims. Further, the sequence listing submitted herewith with the file name P1718-US-2016-08-30-sequence-listing_ST25 is incorporated herein by reference in its entirety.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Yeates, T. O., C. S. Crowley, and S. Tanaka, *Bacterial microcompartment organelles: protein shell structure and evolution*. Annu. Rev. Biophys., 2010. 39: p. 185-205.
2. Yeates, T. O., et al., *Protein-based organelles in bacteria: carboxysomes and related microcompartments*. Nature Reviews Microbiology, 2008. 6(9): p. 681-691.
3. Doherty, A. J., B. A. Connolly, and A. F. Worrall, *Overproduction of the toxic protein, bovine pancreatic*

DNase1, *in Escherichia coli using a tightly controlled T7-promoter-based vector.* Gene, 1993. 136(1): p. 337-340.
4. Dong, H., L. Nilsson, and C. G. Kurland, *Gratuitous overexpression of genes in Escherichia coli leads to growth inhibition and ribosome destruction.* Journal of bacteriology, 1995. 177(6): p. 1497-1504.
5. Chung, B. C., et al., *Crystal structure of MraY, an essential membrane enzyme for bacterial cell wall synthesis.* Science, 2013. 341(6149): p. 1012-1016.
6. Nguyen, L. T., E. F. Haney, and H. J. Vogel, *The expanding scope of antimicrobial peptide structures and their modes of action.* Trends in biotechnology, 2011. 29(9): p. 464-472.
7. Durand, S., et al., *Activation of RegB endoribonuclease by S1 ribosomal protein requires an 11 nt conserved sequence.* Nucleic Acids Res, 2006. 34(22): p. 6549-60.
8. Gaspar, D., A. S. Veiga, and M. A. Castanho, *From antimicrobial to anticancer peptides. A review.* Frontiers in Microbiology, 2013. 4: p. 294.
9. Hoskin, D. W. and A. Ramamoorthy, *Studies on anticancer activities of antimicrobial peptides.* Biochimica et Biophysica Acta (BBA)-Biomembranes, 2008. 1778(2): p. 357-375.
10. Wolfe, M. S., *Intramembrane-cleaving proteases.* Journal of Biological Chemistry, 2009. 284(21): p. 13969-13973.
11. Schmelcher, M., D. M. Donovan, and M. J. Loessner, *Bacteriophage endolysins as novel antimicrobials.* Future microbiology, 2012. 7(10): p. 1147-1171.
12. Wang, G. S., X. Li, and Z. Wang, *APD3: the antimicrobial peptide database as a tool for research and education.* Nucleic Acids Res, 2016. 44(D1): p. D1087-D1093.
13. Marr, A. K., W. J. Gooderham, and R. E. W. Hancock, *Antibacterial peptides for therapeutic use: obstacles and realistic outlook.* Current Opinion in Pharmacology, 2006. 6(5): p. 468-472.
14. Menzella, H. G., *Comparison of two codon optimization strategies to enhance recombinant protein production in Escherichia coli.* Microbial cell factories, 2011. 10(1): p. 1.
15. Parachin, N. S., et al., *Expression systems for heterologous production of antimicrobial peptides.* Peptides, 2012. 38(2): p. 446-456.
16. Berneche, S. and B. Roux, *Energetics of ion conduction through the IC channel.* Nature, 2001. 414(6859): p. 73-77.
17. Parsons, J. B., et al., *Synthesis of empty bacterial microcompartments, directed organelle protein incorporation, and evidence of filament-associated organelle movement.* Mol. Cell, 2010. 38(2): p. 305-15.
18. Sargent, F., et al., *A synthetic system for expression of components of a bacterial microcompartment.* Microbiology, 2013. 159(Pt 11): p. 2427-36.
19. Choudhary, S., et al., *Engineered protein nano-compartments for targeted enzyme localization.* PLoS One, 2012. 7(3): p. e33342.
20. Fan, C. G., et al., *Short N-terminal sequences package proteins into bacterial microcompartments.* Proc. Natl. Acad. Sci. U.S.A., 2010. 107(16): p. 7509-7514.
21. Young, C. L., Z. T. Britton, and A. S. Robinson, *Recombinant protein expression and purification: a comprehensive review of affinity tags and microbial applications.* Biotechnol. J., 2012. 7(5): p. 620-34.
22. Sinha, S., et al., *The PduM Protein Is a Structural Component of the Microcompartments Involved in Coenzyme B-12-Dependent 1,2-Propanediol Degradation by Salmonella enterica.* J. Bacteriol., 2012. 194(8): p. 1912-1918.

The invention claimed is:

1. A method to provide a toxic non-native protein in a cell, the method comprising introducing into the cell at least one first polynucleotide encoding at least one microcompartment protein, the at least one polynucleotide operatively linked to one or more first regulatory elements leading to the expression of the at least one microcompartment protein in the cell, the at least one microcompartment protein capable of assembling with one or more same and/or different microcompartment proteins to form at least one empty microcompartment within the cell; and introducing into the cell at least one second polynucleotide encoding for one or more toxic non-native proteins capable of reacting with a native membrane substrate with a reaction resulting in a cell damage, each of the one or more toxic non-native proteins operably linked to a leader peptide capable of directing expressed proteins to the at least one empty microcompartment, the at least one second polynucleotide operably linked to one or more second regulatory elements leading to the expression of the at least one toxic non-native protein operably linked to the leader peptide in the cell;

to obtain the toxic non-native protein within the at least one empty microcompartment within the cell.

2. The method of claim 1, wherein the native membrane substrate is a substrate located in a plasma membrane, an outer membrane or a cell wall of the cell.

3. The method of claim 1, wherein the native membrane substrate are selected from native membrane lipids, native membrane proteins and native peptidoglycans.

4. The method of claim 1, wherein the one or more non-native toxic proteins comprise at least one non-native antimicrobial peptide.

5. The method of claim 4, wherein the at least one non-native antimicrobial peptide is selected from a cationic antimicrobial peptide capable of reacting with native phospholipids in a plasma membrane of the cell, a cationic antimicrobial peptide capable of reacting with a native outer membrane, and a cationic antimicrobial peptide capable of reacting with a native outer membrane protein.

6. The method of claim 4 wherein the at least one non-native antimicrobial peptide is selected from cecropins, magainins, melittin, protegrins, and nisins.

7. The method of claim 1, wherein the one or more non-native toxic proteins comprise one or more non-native proteases capable of reacting with a native membrane substrate.

8. The method of claim 1, wherein the one or more non-native toxic proteins comprise one or more non-native proteases and one or more of non-native lysins.

9. The method of claim 1, wherein the one or more non-native toxic proteins comprise chemotherapic non-native proteins.

10. The method of claim 1, wherein introducing into the cell the at least one first polynucleotide is performed by introducing an expression vector comprising at least one polynucleotide of the at least one first polynucleotide and the one or more first regulatory elements in a configuration leading to transcription of the microcompartment protein carried on the expression vector.

11. The method of claim 1, wherein introducing into the cell the at least one second polynucleotide encoding for the toxic non-native protein is performed by introducing an expression vector comprising the at least one polynucleotide of the at least one second polynucleotide and the one or more second regulatory elements in a configuration leading to transcription of the toxic non-native protein carried on the expression vector.

12. The method of claim 1, wherein the at least one first polynucleotide comprises one or more polynucleotides encoding for two or more microcompartment proteins.

13. A system for shielding a bacterial cell from toxicity during intracellular production of a toxic non-native protein, the system comprising at least one first polynucleotide encoding at least one microcompartment protein operatively linked to one or more first regulatory elements leading to the expression of the at least one microcompartment protein in the cell, the at least one microcompartment protein capable of assembling with one or more same and/or different microcompartment proteins to form at least one empty microcompartment within the cell; and at least one second polynucleotide encoding for at least one toxic non-native protein capable of reacting with a native membrane substrate with a reaction resulting in a cell damage each of the one or more toxic non-native proteins operably linked to a leader peptide capable of directing expressed proteins to the at least one empty microcompartment, the at least one second polynucleotide operatively linked to one or more second regulatory elements leading to the expression of the at least one toxic non-native protein operably linked to the leader peptide.

14. The system of claim 13, wherein the at least one first polynucleotide and the one or more first regulatory elements are comprised within an expression vector wherein the one or more first regulatory elements and the at least one first polynucleotide are located in a configuration leading to transcription of the at least one microcompartment protein carried on the expression vector.

15. The system of claim 13, wherein the at least one second polynucleotide and one or more second regulatory elements are comprised within an expression vector wherein the at least one second polynucleotide and the one or more second regulatory elements are located in a configuration leading to efficient transcription of the at least one toxic non-native protein carried on the expression vector.

16. The system of claim 13, wherein the one or more first regulatory elements comprise an enhancer and/or an over-expression promoter.

17. The system of claim 13, wherein the one or more second regulatory elements comprise a low-level constitutive promoter.

18. The system of claim 13, wherein the one or more first regulatory elements and/or the one or more second regulatory elements comprise a tunable promoter.

19. The system of claim 13, wherein the at least one first polynucleotide comprises one or more polynucleotides encoding for multiple microcompartment proteins.

20. The system of any of claim 13, wherein the at least one first polynucleotide comprises one or more polynucleotides encoding for PduA, B, J, K, N and U.

21. The system of claim 13, wherein the one or more non-native toxic proteins comprise at least one non-native antimicrobial peptide.

22. The system of claim 13, wherein the at least one non-native antimicrobial peptide is selected from cecropins, magainins, melittin, protegrins, and nisins.

23. The system of claim 13, wherein the one or more non-native toxic proteins comprise one or more non-native proteases capable of reacting with a native membrane substrate.

24. The system of claim 13, wherein the one or more non-native toxic proteins comprise one or more non-native proteases and one or more of non-native lysins.

25. The system of claim 13, wherein the one or more non-native toxic proteins comprise chemotherapic non-native proteins.

26. A cell obtainable by the method of claim 1.

27. A composition comprising one or more cells according to claim 26 together with a suitable vehicle.

* * * * *

SEQUENCE LISTING

```
<160> NUMBER OF SEQ ID NOS: 16

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: X is D or N
<220> FEATURE:
<221> NAME/KEY: MISC_FEATURE
<222> LOCATION: (4)..(4)
<223> OTHER INFORMATION: X is any natural amino acid
<220> FEATURE:
<221> NAME/KEY: MISC_FEATURE
<222> LOCATION: (5)..(5)
<223> OTHER INFORMATION: X is any natural amino acid

<400> SEQUENCE: 1

Ala Xaa Leu Xaa Xaa
1               5

<210> SEQ ID NO 2
<211> LENGTH: 37
<212> TYPE: PRT
<213> ORGANISM: Hyalophora cecropia
```

-continued

<400> SEQUENCE: 2

Lys Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
                20                  25                  30

Thr Gln Ile Ala Lys
        35

<210> SEQ ID NO 3
<211> LENGTH: 35
<212> TYPE: PRT
<213> ORGANISM: Hyalophora cecropia

<400> SEQUENCE: 3

Lys Trp Lys Val Phe Lys Lys Ile Glu Lys Met Gly Arg Asn Ile Arg
1               5                   10                  15

Asn Gly Ile Val Lys Ala Gly Pro Ala Ile Ala Val Leu Gly Glu Ala
                20                  25                  30

Lys Ala Leu
        35

<210> SEQ ID NO 4
<211> LENGTH: 16
<212> TYPE: DNA
<213> ORGANISM: Honey bee

<400> SEQUENCE: 4
ggavkvttga swkrkr                                               16

<210> SEQ ID NO 5
<211> LENGTH: 116
<212> TYPE: DNA
<213> ORGANISM: Artificial Sequence
<220> FEATURE:
<223> OTHER INFORMATION: Synthetic Oligonucleotide

<400> SEQUENCE: 5
aattgtgagc ggataacaat tacgagcttc atgcacagtg aaatcatgaa aaatttattt      60
gctttgtgag cggataacaa ttataatatg tggaattgtg agcgctcaca attcca        116

<210> SEQ ID NO 6
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 6
tttaaggagg taaaaa                                               16

<210> SEQ ID NO 7
<211> LENGTH: 113
<212> TYPE: DNA
<213> ORGANISM: Artificial Sequence
<220> FEATURE:
<223> OTHER INFORMATION: Synthetic Oligonucleotide

<400> SEQUENCE: 7
caccacaatt cagcaaattg tgaacatcat cacgttcatc tttccctggt tgccaatggc      60 ccatttttcct gtcagtaacg agaaggtcgc gaattcaggc gcttttaga ctg           113

```
<210> SEQ ID NO 8
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 8
aggagatata cat                                                          13

<210> SEQ ID NO 9
<211> LENGTH: 111
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(57)
<223> OTHER INFORMATION: Codon-optimized nucleotide sequences for the
      BMC targeting tag
<220> FEATURE:
<221> NAME/KEY: misc_feature
<222> LOCATION: (58)..(69)
<223> OTHER INFORMATION: Codon-optimized nucleotide sequences for the
      FactorXa site
<220> FEATURE:
<221> NAME/KEY: misc_feature
<222> LOCATION: (70)..(75)
<223> OTHER INFORMATION: Codon-optimized nucleotide sequences for the
      BglII site for insertion of desired toxic protein
<220> FEATURE:
<221> NAME/KEY: misc_feature
<222> LOCATION: (76)..(93)
<223> OTHER INFORMATION: Codon-optimized nucleotide sequences for the
      thrombin site
<220> FEATURE:
<221> NAME/KEY: misc_feature
<222> LOCATION: (94)..(110)
<223> OTHER INFORMATION: Codon-optimized nucleotide sequences for the
      His6 tag

<400> SEQUENCE: 9
atggaccaga acaaattga agaaattgtg cgtagcgtta tggcgtccat gggtcagatc         60
gagggtcgta gatctctggt cccgcgtggc agccaccacc atcatcacca c                111

<210> SEQ ID NO 10
<211> LENGTH: 113
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(60)
<223> OTHER INFORMATION: Codon-optimized nucleotide sequences for the
      BMC targeting tag
<220> FEATURE:
<221> NAME/KEY: misc_feature
<222> LOCATION: (61)..(72)
<223> OTHER INFORMATION: Codon-optimized nucleotide sequences for the
      FactorXa site
<220> FEATURE:
<221> NAME/KEY: misc_feature
<222> LOCATION: (73)..(78)
<223> OTHER INFORMATION: Codon-optimized nucleotide sequences for the
      BglII site for insertion of desired toxic protein
<220> FEATURE:
<221> NAME/KEY: misc_feature
<222> LOCATION: (73)..(91)
<223> OTHER INFORMATION: Codon-optimized nucleotide sequences for the
      Thrombin site
```

<220> FEATURE:
<221> NAME/KEY: misc_feature
<222> LOCATION: (92)..(113)
<223> OTHER INFORMATION: Codon-optimized nucleotide sequences for the
      His6 tag

<400> SEQUENCE: 10
atggaaatca cgaaaagct gctgcgtcag attattgaag atgtgttgcg cgacatgaaa      60
atcgagggtc gtagatctct ggttccgcgt ggcagccatc accaccacca cac            113

<210> SEQ ID NO 11
<211> LENGTH: 107
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(24)
<223> OTHER INFORMATION: Codon-optimized nucleotide sequences for the
      BMC targeting tag
<220> FEATURE:
<221> NAME/KEY: misc_feature
<222> LOCATION: (25)..(36)
<223> OTHER INFORMATION: Codon-optimized nucleotide sequences for the
      FactorXa site

<400> SEQUENCE: 11
atgaacacga gcgagctgga aaccctgatc cgtaccattt tgagcgaaca gctgtcgagg      60
gtcgcagatc tctggttccg cgtggctccc accatcacca ccatcac                   107

<210> SEQ ID NO 12
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 12

Met Asn Thr Ser Glu Leu Glu Thr Leu Ile Arg Thr Ile Leu Ser Glu
1               5                   10                  15

Gln Leu

<210> SEQ ID NO 13
<211> LENGTH: 20
<212> TYPE: PRT
<213> ORGANISM: Artificial Sequence
<220> FEATURE:
<223> OTHER INFORMATION: Synthetic Peptide

<400> SEQUENCE: 13

Met Glu Ile Asn Glu Lys Leu Leu Arg Gln Ile Ile Glu Asp Val Leu
1               5                   10                  15

Arg Asp Met Lys
            20

<210> SEQ ID NO 14
<211> LENGTH: 19
<212> TYPE: PRT
<213> ORGANISM: Artificial Sequence
<220> FEATURE:
<223> OTHER INFORMATION: Synthetic Peptide

```
<400> SEQUENCE: 14

Met Asp Gln Lys Gln Ile Glu Glu Ile Val Arg Ser Val Met Ala Ser
1               5                   10                  15

Met Gly Gln

<210> SEQ ID NO 15
<211> LENGTH: 129
<212> TYPE: PRT
<213> ORGANISM: Artificial Sequence
<220> FEATURE:
<223> OTHER INFORMATION: Synthetic Peptide

<400> SEQUENCE: 15

Met Asn Thr Ser Glu Leu Glu Thr Leu Ile Arg Thr Ile Leu Ser Glu
1               5                   10                  15

Gln Leu Ile Glu Gly Arg Arg Ser Met Val Arg Trp Thr Leu Trp Asp
                20                  25                  30

Thr Leu Ala Phe Leu Leu Leu Leu Ser Leu Leu Leu Pro Ser Leu Leu
            35                  40                  45

Ile Met Phe Ile Pro Ser Thr Phe Lys Arg Pro Val Ser Ser Trp Lys
    50                  55                  60

Ala Leu Asn Leu Arg Lys Thr Leu Leu Met Ala Ser Ser Val Arg Leu
65                  70                  75                  80

Lys Pro Leu Asn Cys Ser Arg Leu Pro Cys Val Tyr Ala Gln Glu Thr
                85                  90                  95

Leu Thr Phe Leu Leu Thr Gln Lys Lys Thr Cys Val Lys Asn Tyr Val
            100                 105                 110

Arg Lys Glu Arg Ser Leu Val Pro Arg Gly Ser His His His His His
        115                 120                 125

His

<210> SEQ ID NO 16
<211> LENGTH: 127
<212> TYPE: PRT
<213> ORGANISM: Artificial Sequence
<220> FEATURE:
<223> OTHER INFORMATION: Synthetic Peptide

<400> SEQUENCE: 16

Met Asn Thr Ser Glu Leu Glu Thr Leu Ile Arg Thr Ile Leu Ser Glu
1               5                   10                  15

Gln Leu Ile Glu Gly Arg Met Val Arg Trp Thr Leu Trp Asp Thr Leu
                20                  25                  30

Ala Phe Leu Leu Leu Leu Ser Leu Leu Leu Pro Ser Leu Leu Ile Met
            35                  40                  45

Phe Ile Pro Ser Thr Phe Lys Arg Pro Val Ser Ser Trp Lys Ala Leu
    50                  55                  60

Asn Leu Arg Lys Thr Leu Leu Met Ala Ser Ser Val Arg Leu Lys Pro
65                  70                  75                  80

Leu Asn Cys Ser Arg Leu Pro Cys Val Tyr Ala Gln Glu Thr Leu Thr
                85                  90                  95

Phe Leu Leu Thr Gln Lys Lys Thr Cys Val Lys Asn Tyr Val Arg Lys
            100                 105                 110

Glu Arg Ser Leu Val Pro Arg Gly Ser His His His His His
        115                 120                 125
```